(12) United States Patent
Eppler et al.

(10) Patent No.: US 10,071,034 B2
(45) Date of Patent: Sep. 11, 2018

(54) SOLVENT COMPOSITIONS

(71) Applicant: Amyris, Inc., Emeryville, CA (US)

(72) Inventors: Ross Keating Eppler, Emeryville, CA (US); Karl Fisher, Emeryville, CA (US); Roberto Vazquez, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 189 days.

(21) Appl. No.: 14/702,607

(22) Filed: May 1, 2015

(65) Prior Publication Data

US 2015/0315520 A1 Nov. 5, 2015

Related U.S. Application Data

(60) Provisional application No. 61/988,053, filed on May 2, 2014, provisional application No. 61/994,389, filed on May 16, 2014, provisional application No. 62/052,397, filed on Sep. 18, 2014.

(51) Int. Cl.
| | | |
|---|---|---|
| *A61K 8/31* | (2006.01) | |
| *A61Q 19/00* | (2006.01) | |
| *A61Q 1/04* | (2006.01) | |
| *A61Q 5/00* | (2006.01) | |
| *C11D 3/18* | (2006.01) | |
| *A61Q 5/06* | (2006.01) | |

(52) U.S. Cl.
CPC .................. *A61K 8/31* (2013.01); *A61Q 1/04* (2013.01); *A61Q 5/00* (2013.01); *A61Q 5/065* (2013.01); *A61Q 19/00* (2013.01); *C11D 3/184* (2013.01)

(58) Field of Classification Search
CPC ... A61K 8/31; A61Q 1/04; A61Q 5/00; A61Q 5/065; A61Q 19/00; C11D 3/184
See application file for complete search history.

(56) References Cited

U.S. PATENT DOCUMENTS 5,786,310 A 7/1998 Dubief et al.
8,519,204 B2 8/2013 Ohler et al.

FOREIGN PATENT DOCUMENTS

| CA | 2862593 | 8/2015 |
| EP | 0 007 076 | 1/1980 |
| FR | 2 596 061 | 9/1987 |
| JP | 2012233281 | 11/2012 |
| WO | WO-2012/141783 | 10/2012 |
| WO | WO-2012/141784 | 10/2012 |

OTHER PUBLICATIONS

Sigma-Aldrich (https://www.sigmaaldrich.com/catalog/product/aldrich/124249?lang=en&region=US, Accessed Dec. 5, 2017, pp. 1-3).*
International Search Report and Written Opinion dated Aug. 3, 2015 for PCT/US2015/028954 filed May 1, 2015, 13 pages.
Schneiderman et al. "Juvenile Hormone Activity of Structurally Unrelated Compounds", *Journal of Insect Physiology*, Jan. 1965, vol. 11, pp. 1641-1649.
Farmer et al. "Rubber, Polyisoprene and Allied Compounds. Part I. The Synthesis of Low-Molecular Polyisoprenes of the Rubber and the Squalene Type", *Journal of the Chemical Society, Chemical Society, Letchworth*; Jan. 1942, pp. 116-121, XP008141093.
Database WPI, *Thomson Scientific, London*, AN 1993-224472, XP002741774; and JP H05 148499, Jun. 1993, abstract.

* cited by examiner

*Primary Examiner* — Alma Pipic
(74) *Attorney, Agent, or Firm* — Squire Patton Boggs (US) LLP

(57) ABSTRACT

Provided herein are compositions comprising partially hydrogenated farnesene. In certain embodiments, the compositions are useful as solvents, degreasers, cleaning products, personal care products, and for other uses. Also provided herein are methods of making the compositions and methods of their use.

38 Claims, 11 Drawing Sheets

SOLVENT COMPOSITIONS

CROSS REFERENCE TO RELATED APPLICATIONS

This application claims benefit of priority to U.S. Provisional Patent Application No. 61/988,053, filed May 2, 2014, U.S. Provisional Patent Application No. 61/994,389, filed May 16, 2014, and U.S. Provisional Patent Application No. 62/052,397, filed Sep. 18, 2014, which are incorporated herein by reference.

FIELD

Provided herein are compositions comprising partially hydrogenated farnesene, methods of their use and methods of their production. In certain embodiments, the compositions are useful as solvents such as cleaning solvents and degreasers. In certain embodiments, the compositions are useful as personal care products.

BACKGROUND

Many commercially available consumer products contain solvents that include volatile organic compounds (VOCs), which are environmentally unfriendly. The U.S. Environmental Protection Agency and state agencies have issued regulations to reduce VOC emissions from a variety of products. VOCs have been determined to be a major contributing factor to the formation of ground-level ozone, which has been proven to be a public health concern. In order to reduce ozone levels, the regulations limit the amount and classes of VOCs that can be used in various categories of products such as solvent compositions and cleaning product formulations. The VOC limitations issued by various authorities are constantly evolving and becoming more restrictive.

Solvent compositions are useful in our daily lives for removing organic and other substances from surfaces of furniture, floors, walls, mechanical devices, automobiles, bicycles, clothing, skin and the like. Useful solvents have advantageous properties, such as vapor pressures, viscosities, degreasing powers, stabilities, odor and/or color. For many applications, advantageous safety profiles are desired. Solvent compositions with low environmental impact and low VOC content are needed, and few solvent compositions have been provided from sustainable, renewable sources.

Therefore, there is a continuing need for new solvent compositions with desired properties, if possible, from sustainable, renewable sources. Also, there is a need to improve solvent compositions that meet low VOC emission standards and that are environmentally friendly.

SUMMARY

Provided herein are compositions useful as solvents, methods of their use, and methods of their production. In certain embodiments, the compositions display advantageous solvency, advantageous stability, and/or advantageous safety properties. In certain embodiments, the compositions have low-flash points and are non-flammable. In certain embodiments, the compositions are free or substantially free of sulfur, and have low odor and color. In some embodiments, the compositions provided herein have emollient properties, which are desirable in personal care products. In particularly advantageous embodiments, the compositions are produced from sustainable, renewable sources.

The compositions and products provided herein also have excellent environmental profile, for example low VOC content, without compromising cleaning efficiencies or other performance properties in comparison to other commercially available products. In certain embodiments, the compositions and products provided herein are VOC exempt. A composition is considered a VOC exempt organic solvent if it meets one of the following criteria: (1) it has a vapor pressure less than 0.1 mmHg at 20° C., as determined by ARB Method 310; or (2) it is a chemical compound with more than 12 carbon atoms, or a chemical mixture comprised solely of compounds with more than 12 carbon atoms, and the vapor pressure is unknown; or (3) it is a chemical compound with a boiling point greater than 216° C. as determined by ARB Method 310. Thus, the compositions provided herein can be used to replace or supplement existing organic solvents, such as d-limonene, to improve the VOC emission profile and other properties of end products.

In one aspect, provided herein are compositions comprising partially hydrogenated farnesene. In an embodiment, the compositions comprise a high percentage of dihydrofarnesene. Dihydrofarnesene has one hydrogenated double bond. The compositions further comprise a tetrahydrofarnesene, typically in an amount less than the amount of dihydrofarnesene. Tetrahydrofarnesene has two hydrogenated double bonds. The compositions can further comprise hexahydrofarnesene and/or farnesane, typically in amounts less than the dihydrofarnesene and tetrahydrofarnesene. Hexahydrofarnesene has three hydrogenated double bonds, and farnesane is fully hydrogenated (no double bonds).

In certain embodiments, a composition comprises about 78 wt. % to about 85 wt. % dihydrofarnesene and about 20 wt. % to about 14 wt. % tetrahydrofarnesene, compared to the total amount of farnesene and farnesene derivatives in the composition. In certain embodiments, the composition comprises about 83 wt. % to about 85 wt. % dihydrofarnesene and about 16 wt. % to about 14 wt. % tetrahydrofarnesene, compared to the total amount of farnesene and farnesene derivatives in the composition. In certain embodiments, a composition comprises about 78 wt. % to about 97 wt. % dihydrofarnesene and about 20 wt. % to about 2 wt. % tetrahydrofarnesene, compared to the total amount of farnesene and farnesene derivatives in the composition. In certain embodiments, a composition comprises about 83 wt. % to about 97 wt. % dihydrofarnesene and about 16 wt. % to about 2 wt. % tetrahydrofarnesene, compared to the total amount of farnesene and farnesene derivatives in the composition. In certain embodiments, a composition comprises about 96 wt. % dihydrofarnesene, compared to the total amount of farnesene and farnesene derivatives in the composition.

In certain embodiments, a composition further comprises about 0.1 wt. % to about 2 wt. % hexahydrofarnesene, compared to the total amount of farnesene and farnesene derivatives in the composition.

In certain embodiments, the composition further comprises less than about 0.1 wt. % farnesane, compared to the total amount of farnesene and farnesene derivatives in the composition.

In certain embodiments, the composition comprises less than about 0.25 wt. % bisbolene, compared to the total amount of farnesene and farnesene derivatives in the composition.

In certain embodiments, the composition comprises, on average, about 1.0 to about 1.4 double bonds per molecule of farnesene or farnesene derivative in the composition. In other words, the ratio of the total number of double bonds of farnesene and farnesene derivative molecules in the composition versus the total number of farnesene and farnesene derivative molecules in the composition is about 1.0 to about 1.4. In certain embodiments, the composition comprises, on average, about 1.0 to about 1.25 double bonds per molecule of farnesene and farnesene derivative in the composition. In certain embodiments, the composition comprises, on average, about 1.1 to about 1.2 double bonds per molecule of farnesene and farnesene derivative in the composition. In certain embodiments, the composition comprises, on average, about 1.04 to about 1.16 double bonds per molecule of the farnesene and farnesene derivatives in the composition.

In another aspect, the composition comprises about 60 wt. % to about 100 wt. % dihydrofarnesene, compared to the total amount of farnesene and farnesene derivatives in the composition. In certain embodiments, the composition further comprises at least one of a co-solvent, surfactant, water, emulsifier, emollient, thickener, additive, or a mixture thereof.

In certain embodiments, the composition further comprises a co-solvent. In some embodiments, the co-solvent is selected from the group consisting of limonene, benzene, high flash aromatic naphtha, soy methyl ester, ethyl lactate, paraffins, dibasic esters, propylene glycol, ethyl alcohol, and a mixture thereof.

In certain embodiments, the composition further comprises a surfactant. In some embodiments, the surfactant is selected from the group consisting of sodium lauryl ether sulfate, ethoxylated alcohol surfactant, fatty acid diethanolamine, orange oil emulsifier, acrylate-based emulsion copolymer, polyoxyethers of lauryl alcohol, linear isopropylamine dodecylbenzene sulfonate, blended alcohol ethoxylate, alkoxylated alcohol, sodium iminodipropionate, nonionic alcohol ethoxylates, a palm kernel alcohol ethoxylated and propoxylated surfactant, sodium xylene sulfonate, and a mixture thereof.

In certain embodiments, the composition further comprises water.

In certain embodiments, the composition further comprises an emulsifier. In some embodiments, the emulsifier is selected from the group consisting of lauryl alcohol, fatty acid diethanolamine, ammonium methyl sulfate and fatty alcohol ethoxylate, linear alcohol ethoxylate, sodium branched dodecyl benzene sulfonate, and a mixture thereof.

In certain embodiments, the composition further comprises an emollient. In some embodiments, the emollient is selected from the group consisting of fatty acids, alkyl ethoxylates, fatty acid ester ethoxylates, fatty alcohols, polysiloxanes, mucopolysaccharides, polyols, polysaccharides, urea derivatives, PPG-3 benzyl ether myristate, hydrogenated polyisobutene, butylene/ethylene/styrene copolymer, ethylene/propylene/styrene copolymer, bis-diglyceryl polyacyladipate-2, pentaerythrityl tetraisostearate, $C_{10-30}$ cholesterol/lanosterol esters, or a mixture thereof.

In certain embodiments, the composition further comprises a thickener. In some embodiments, the thickener is selected from the group consisting of cellulosic thickeners, natural gums, acrylates, starches, stearates, fatty acid alcohols, clays, salts, candelilla wax, carnauba wax, beeswax, oils, linear alcohol ethoxylates, and a mixture thereof.

In certain embodiments, the composition further comprises at least one additive. In some embodiments, the at least one additive is selected from the group consisting of a buffering agent, pH control agent, fragrance, flavor, defoamer, dye, whitener, brightener, solubilizing material, stabilizer, thickener, corrosion inhibitors, lotions, mineral oils, enzymes, cloud point modifiers, preservative, ion exchanger, chelating agent, sudsing control agent, soil removal agent, softening agent, opacifier, inert diluent, graying inhibitor, polymer, abrasive, exfoliant, and a mixture thereof.

In another aspect, provided herein are kits comprising the present partially hydrogenated compositions described herein, and instructions for using the compositions.

In another aspect, provided herein are methods of producing a composition, wherein the method comprises (a) reacting a composition comprising farnesene with hydrogen in the presence of a hydrogenation catalyst to produce a composition comprising about 60 wt. % to about 100 wt. % dihydrofarnesene, compared to the total amount of farnesene and farnesene derivatives in the composition; and (b) filtering products of step (a) using an adsorbent to remove small, volatile, organic oxygenate compounds. In certain embodiments, the method further comprises, after step (b), adding a stabilizer to the composition, wherein the stabilizer, which, when oxidized, does not form a quinone. In certain embodiments, the adsorbent comprises alumina, silica, or a mixture thereof. In certain embodiments, the small, volatile, organic oxygenate compounds filtered in step (b) are $C_4$ to $C_{10}$ compounds. In certain embodiments, a composition produced by the method is provided, wherein the composition is substantially free of small, volatile organic oxygenate compounds. The composition produced by the method can further comprise a stabilizer, which, when oxidized, does not change color or form a quinone.

In another aspect, provided herein are compositions comprising about 78 wt. % to about 97 wt. % dihydrofarnesene and about 20 wt. % to about 2 wt. % tetrahydrofarnesene, compared to the total amount of farnesene and farnesene derivatives in the composition. In some embodiments, the compositions further comprise a stabilizer, which, when oxidized, does not form a quinone. In certain embodiments, the stabilizer is butylated hydroxytoluene. In certain embodiments, the stabilizer is present at a concentration of about 100 to 500 ppm in the composition. In certain embodiments, the composition is substantially free of $C_4$ to $C_{10}$ volatile, organic oxygenate compounds. These odor causing impurities can be filtered out using adsorbents. In certain embodiments, the compositions further comprise at least one of a co-solvent, surfactant, water, emulsifier, emollient, thickener, or a mixture thereof.

In another aspect, provided herein are products comprising the compositions. Useful products include solvents, degreasers, cleaning products, personal care products, and the like. In a further aspect, provided herein are methods of making and using the compositions. The compositions can be used, for example, for cleaning, for degreasing, and for any other application deemed useful to the practitioner in the art.

DESCRIPTION OF EXEMPLARY EMBODIMENTS

Figure 1:
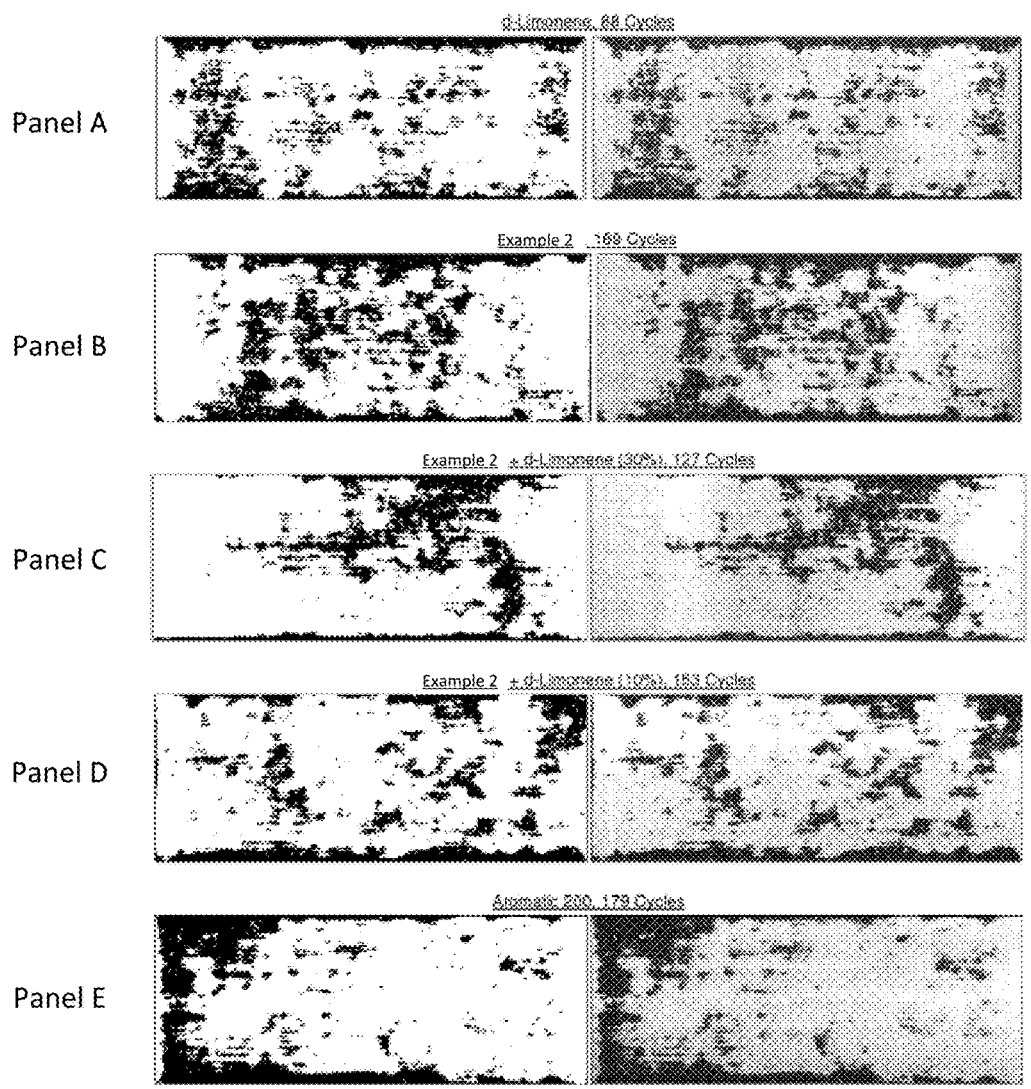
FIG. 1, panels A through I, provide asphalt washing camera images (right panels) and images after processing with image analysis software (left panels).
Figure 1:
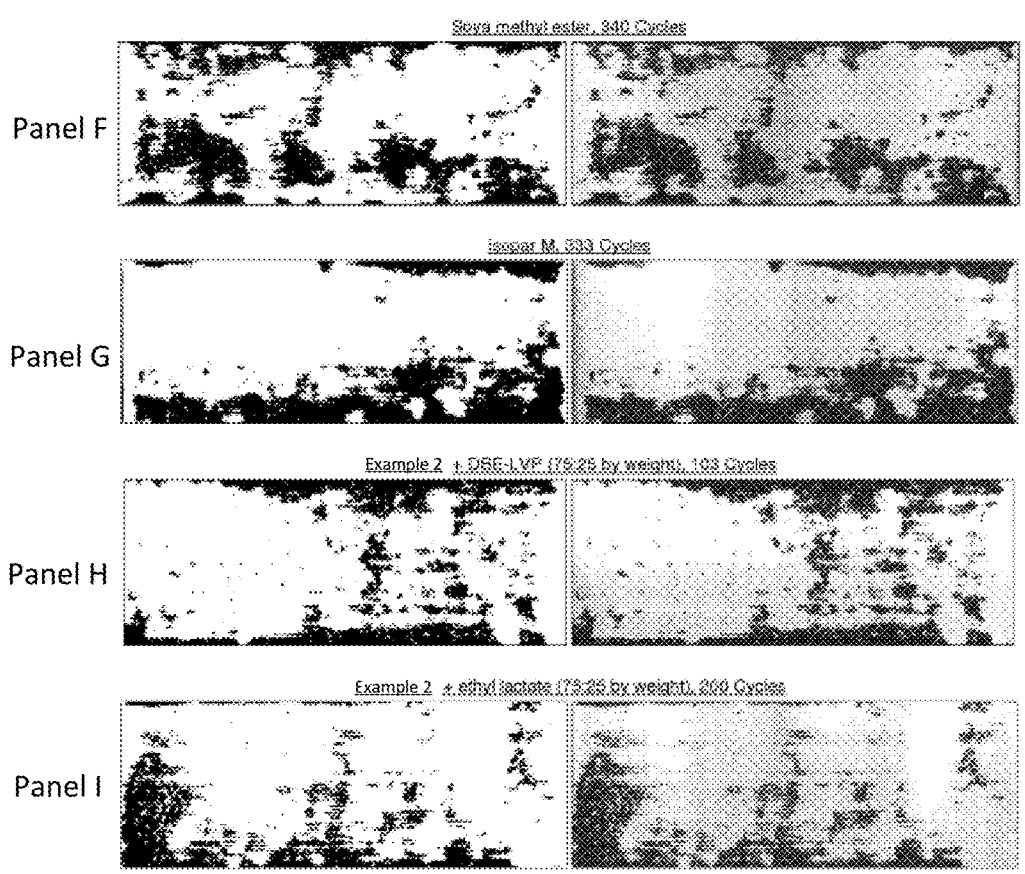

Provided herein are compositions useful as solvents, methods of their use and methods of their production.

DEFINITIONS

When referring to the compounds, compositions and methods provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

"Farnesene" as used herein refers to α-farnesene, β-farnesene or a mixture thereof "α-farnesene" refers to a compound having the following structure:

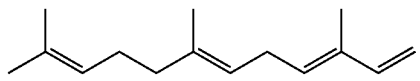

or a stereoisomer thereof. "β-farnesene" refers to a compound having the following structure:

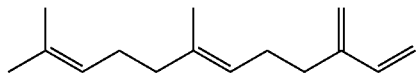

or a stereoisomer thereof. In some variations, β-farnesene comprises a substantially pure stereoisomer of β-farnesene. In other variations, β-farnesene comprises a mixture of stereoisomers, such as cis-trans isomers. In some variations, the amount of each of the stereoisomers in a β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, with respect to the total weight of the β-farnesene mixture.

"Farnesane" refers to a compound having the following structure:

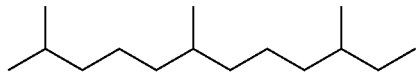

or a stereoisomer thereof.

"Hydrogenated farnesene" refers to farnesene (e.g., β-farnesene) wherein at least one carbon-carbon double bond is hydrogenated. Hydrogenated farnesene encompasses, for example, β-farnesene in which one, two, three or four double bonds are hydrogenated. Hydrogenated farnesene is obtained by complete or partial hydrogenation of farnesene, and encompasses farnesane.

"Partially hydrogenated farnesene" refers to farnesene (e.g., β-farnesene) wherein one, two, or three double bonds are hydrogenated. Partially hydrogenated farnesene can be obtained by partial hydrogenation of farnesene. In some embodiments, a composition comprising partially hydrogenated farnesene, for example obtained by partial hydrogenation of farnesene, may include amounts of farnesene and/or farnesane in addition to one or more of dihydrofarnesene, tetrahydrofarnesene and hexahydrofarnesene.

"Total farnesene/farnesane" refers to the total amount of farnesene and farnesene derivative molecules in a composition. Farnesene derivatives include dihydrofarnesene, tetrahydrofarnesene, hexahydrofarnesene, and farnesane, and multimers thereof, as well as multimers of farnesene. Farnesene derivatives can further include reactive derivatives of farnesene and/or farnesane. These include oxidative derivatives, hydroxyl derivatives such as farnesol, epoxy derivatives, and other derivatives of farnesene and/or farnesane recognized by those skilled in the art. In some embodiments, a composition comprising partially hydrogenated farnesene (also referred to as "a partially hydrogenated farnesene composition") comprises farnesene and farnesene derivatives.

As used herein, % refers to % measured as wt. % or as area % by GC-MS or GC-FID, unless specifically indicated otherwise.

The term "substantially free of" or "substantially in the absence of," when used in connection with an article (including, but not limited to, a compound or composition comprising a compound), refers to the article that includes at least 85% or 90% by weight, in certain embodiments, 95%, 98%, 99%, or 100% by weight, of the designated article. For example, the term "substantially free of" or "substantially in the absence of" with respect to a farnesene composition can refer to a solvent composition that includes at least 85% or 90% by weight, in certain embodiments, 95%, 98%, 99%, or 100% by weight, of a designated isomer of farnesene. In certain embodiments, in the methods, compositions and compounds provided herein, the compounds are substantially free of undesignated isomers. In another example, the term "substantially free" with respect to small, volatile, organic oxygenate compounds can refer to compositions or articles having less than 0.01 wt. % by weight of these compounds based on the total weight of the composition, or undetectable by GC-MS or GC-FID.

Similarly, the term "isolated" with respect to a farnesene composition refers to a farnesene composition that includes at least 85%, 90%, 95%, 98%, or 99% to 100% by weight, of a designated farnesene isomer, the remainder comprising other chemical species or isomers, compounds, solvents, and/or other impurities.

In the following description, all numbers disclosed herein are approximate values, regardless of whether the word "about" or "approximate" is used in connection therewith. Numbers may vary by 1%, 2%, 5%, or by 10 to 20%. Whenever a numerical range with a lower limit $R^L$ and an upper limit $R^U$ is disclosed, any number falling within the range is specifically disclosed. In particular, the following numbers $R_k$ within the range are specifically disclosed: $R_k = R^L + k^*(R^U - R^L)$, wherein k is a variable ranging from 0.01 to 1 with a 0.01 increment, i.e., k is 0.01, 0.02, 0.03, 0.04, 0.05, . . . , 0.5, 0.51, 0.52, . . . , 0.95, 0.96, 0.97, 0.98, 0.99, or 1. Further, any numerical range defined by any two numbers $R_k$ as defined above is also specifically disclosed herein.

The term "solvent" refers to a fluid matrix, for example, a liquid substance, in which another substance, such as soils or particulates, is capable of being dispersed or solubilized.

The term "co-solvent" refers to an additional solvent that is useable with a primary solvent to solubilize soils or particulates.

The term "surfactant" or "surface active agent" refers to a substance that reduces surface tension when dissolved in water or aqueous solutions, or which reduces interfacial tension between two liquids, or between a liquid and a solid.

The term "detergent" is generally defined as a substance that reduces the surface tension of water, specifically a surface active agent which concentrates at oil-water interfaces, exerts emulsifying action, and thus aids in removing soils. The detergents may include, for example, traditional sodium and potassium soaps of fatty acids (e.g., anionic surfactants), and synthetic detergents.

The term "emulsifier" refers to a component that reduces the tendency of one or more other components in a composition to phase separate from the composition. The emulsifier aids the dispersal of oil (in the case of oil-in-water emulsions) and water (in the case of water-in-oil emulsions), respectively, into droplets of a small size and helps to maintain the particles in a dispersed state.

As used herein, the terms "detergent" and "emulsifier" refer to substances in the meaning of the above-given definitions and can also be regarded as a class of surfactants, which come in many different forms.

The term "hydrotrope" refers to a compound that is soluble in the water phase of a formulation and that functions to solubilize surfactants in the water phase.

The term "emollient" is a material that softens, coats, lubricates, or moisturizes the substrate (e.g., skin, hair, or nails). The term emollient includes, but is not limited to, conventional lipids materials (e.g., fats, waxes), polar lipids (lipids that have been modified to be more water soluble), silicones, hydrocarbons, and other solvent materials.

The term "thickener" refers to a compound that when added to a liquid composition causes the viscosity of that composition to substantially increase.

The term "carrier" refers to a liquid substance that supports another substance.

The term "diluent" refers to a diluting agent added to a composition to improve the consistence and applicability of the composition to which it is added.

The term "cleaning product" refers to a substance in any suitable form, such as a liquid, suspension, semi-liquid, cream, lotion, semi-solid, or the like, used to remove soils, particulates, or any foreign substance from a surface. As used herein, a cleaning product can include a degreaser, a concentrated cleaning product which is diluted for use, a cleaning product ready for end use for cleaning any suitable surfaces. As used herein, a cleaning product may also include a wipe that is impregnated or pre-moistened with a composition, solvent, degreaser, or cleaning product described herein.

The term "degreaser" refers to a substance for removing all manners of contaminants from solid surfaces, such as oil, greaser, welding flux, water surfactants, metal salts, and the like.

The term "personal care product" refers to a substance in any suitable form, such as liquid, suspension, semi-liquid, cream, lotion, semi-sold, solid, impregnated substrate, or the like that can be topically applied to a consumer (e.g., skin, hair, or nails).

Compositions

In one aspect, provided herein are compositions comprising partially hydrogenated farnesene. In certain embodiments, the compositions are useful as solvents, for example, degreasers. In certain embodiments, the compositions can be used directly as solvents, or in other embodiments, can be used in combination with one or more co-solvents or other components/additives.

In any of the embodiments described herein, the partially hydrogenated farnesene may be produced using renewable resources. For example, the farnesene used in any one of the embodiments described herein can be made from microorganisms, including bioengineered microorganisms, using a renewable carbon source. In particular embodiments, farnesene can be derived from a renewable carbon source using genetically modified microbial cells as described in U.S. Pat. Nos. 7,659,097 B2, 7,399,323 B2, 7,846,222 B2, 8,257,957 B2 or International Patent Publication WO 2007/139924 A2, each of which is incorporated herein by reference in its entirety.

In certain embodiments, the compositions comprise a high amount of dihydrofarnesene. The dihydrofarnesene can be analogous to or derived from α-farnesene or β-farnesene. In certain embodiments, the farnesene is β-farnesene. In the dihydrofarnesenes, any double bond can be hydrogenated. In preferred embodiments, the hydrogenated double bond is one of the conjugated double bonds at the right side of the farnesene molecule, as depicted above (i.e. the α or γ double bond, or the 1 or 3 double bond). In such embodiments, the conjugation is broken. In the farnesene structures above, the α-double bond is depicted at the right side of the molecule.

In useful embodiments, the amount of dihydrofarnesene is sufficient to give the composition a desired solvency. In particular embodiments, the amount of dihydrofarnesene is from about 60 wt. % to about 100 wt. % of the composition. In particular embodiments, the amount of dihydrofarnesene is from about 60 wt. % to about 100 wt. %, compared to the total amount of farnesene and farnesene derivatives in the composition. In particular embodiments, the amount of dihydrofarnesene is from about 65 wt. % to about 100 wt. % of the composition. In particular embodiments, the amount of dihydrofarnesene is from about 65 wt. % to about 100 wt. %, compared to the total amount of farnesene and farnesene derivatives in the composition. In particular embodiments, the amount of dihydrofarnesene is from about 70 wt. % to about 100 wt. % of the composition. In particular embodiments, the amount of dihydrofarnesene is from about 70 wt. % to about 100 wt. %, compared to the total amount of farnesene and farnesene derivatives in the composition. In particular embodiments, the amount of dihydrofarnesene is from about 75 wt. % to about 100 wt. % of the composition. In particular embodiments, the amount of dihydrofarnesene is from about 75 wt. % to about 100 wt. %, compared to the total amount of farnesene and farnesene derivatives in the composition. In particular embodiments, the amount of dihydrofarnesene is from about 75 wt. % to about 90 wt. % of the composition. In particular embodiments, the amount of dihydrofarnesene is from about 75 wt. % to about 90 wt. %, compared to the total amount of farnesene and farnesene derivatives in the composition. In particular embodiments, the amount of dihydrofarnesene is from about 77 wt. % to about 87 wt. % of the composition. In particular embodiments, the amount of dihydrofarnesene is from about 77 wt. % to about 87 wt. %, compared to the total amount of farnesene and farnesene derivatives in the composition. In particular embodiments, the amount of dihydrofarnesene is from about 78 wt. % to about 85 wt. % of the composition. In particular embodiments, the amount of dihydrofarnesene is from about 78 wt. % to about 85 wt. %, compared to the total amount of farnesene and farnesene derivatives in the composition. In particular embodiments, the amount of dihydrofarnesene is from about 79 wt. % to about 85 wt. % of the composition. In particular embodiments, the amount of dihydrofarnesene is from about 79 wt. % to about 85 wt. %, compared to the total amount of farnesene and farnesene derivatives in the composition. In particular embodiments, the amount of dihydrofarnesene is from about 80 wt. % to about 85 wt. % of the composition. In particular embodiments, the amount of dihydrofarnesene is from about 80 wt. % to about 85 wt. %, compared to the total amount of farnesene and farnesene derivatives in the composition. In particular embodiments, the amount of dihydrofarnesene is from about 81 wt. % to about 85 wt. % of the composition. In particular embodiments, the amount of dihydrofarnesene is from about 81 wt. % to about 85 wt. %, compared to the total amount of farnesene and farnesene derivatives in the composition. In particular embodiments, the amount of dihydrofarnesene is from about 82 wt. % to about 85 wt. % of the composition. In particular embodiments, the amount of dihydrofarnesene is from about 82 wt. % to about 85 wt. %, compared to the total amount of farnesene and farnesene derivatives in the composition. In particular embodiments, the amount of dihydrofarnesene is from about 83 wt. % to about 85 wt. % of the composition. In particular embodiments, the amount of dihydrofarnesene is from about 83 wt. % to about 85 wt. %, compared to the total amount of farnesene and farnesene derivatives in the composition. In particular embodiments, the amount of dihydrofarnesene is from about 84 wt. % to about 85 wt. % of the composition. In particular embodiments, the amount of dihydrofarnesene is from about 84 wt. % to about 85 wt. %, compared to the total amount of farnesene and farnesene derivatives in the composition. In particular embodiments, the amount of dihydrofarnesene is from about 78 wt. % to about 97 wt. % of the composition. In particular embodiments, the amount of dihydrofarnesene is from about 78 wt. % to about 97 wt. %, compared to the total amount of farnesene and farnesene derivatives in the composition. In particular embodiments, the amount of dihydrofarnesene is from about 83 wt. % to about 97 wt. % of the composition. In particular embodiments, the amount of dihydrofarnesene is from about 83 wt. % to about 97 wt. %, compared to the total amount of farnesene and farnesene derivatives in the composition. In particular embodiments, the amount of dihydrofarnesene is about 96 wt. % of the composition. In particular embodiments, the amount of dihydrofarnesene is about 96 wt. %, compared to the total amount of farnesene and farnesene derivatives in the composition.

In certain embodiments, the remainder of the farnesene content is mostly tetrahydrofarnesene. The tetrahydrofarnesene can be analogous to or derived from α-farnesene or β-farnesene, where the distinction is appropriate. In certain embodiments, the farnesene is β-farnesene, again where the distinction is appropriate. In the tetrahydrofarnesenes, any two double bonds can be hydrogenated. In preferred embodiments, at least one hydrogenated double bond is one of the conjugated double bonds at the right side of the farnesene molecule, as depicted above (i.e., the α or γ double bond, or the 1 or 3 double bond). In such embodiments, the conjugation is broken. In the farnesene structures above, the α-double bond is depicted at the right side of the molecule.

In particular embodiments, the amount of tetrahydrofarnesene is from about 35 wt. % to about 0 wt. %. In particular embodiments, the amount of tetrahydrofarnesene is from about 35 wt. % to about 0 wt. %, compared to the total amount of farnesene and farnesene derivatives in the composition. In particular embodiments, the amount of tetrahydrofarnesene is from about 20 wt. % to about 14 wt. %. In particular embodiments, the amount of tetrahydrofarnesene is from about 20 wt. % to about 14 wt. %, compared to the total amount of farnesene and farnesene derivatives in the composition. In particular embodiments, the amount of tetrahydrofarnesene is from about 19 wt. % to about 14 wt. %. In particular embodiments, the amount of tetrahydrofarnesene is from about 19 wt. % to about 14 wt. %, compared to the total amount of farnesene and farnesene derivatives in the composition. In particular embodiments, the amount of tetrahydrofarnesene is from about 18 wt. % to about 14 wt. %. In particular embodiments, the amount of tetrahydrofarnesene is from about 18 wt. % to about 14 wt. %, compared to the total amount of farnesene and farnesene derivatives in the composition. In particular embodiments, the amount of tetrahydrofarnesene is from about 17 wt. % to about 14 wt. %. In particular embodiments, the amount of tetrahydrofarnesene is from about 17 wt. % to about 14 wt. %, compared to the total amount of farnesene and farnesene derivatives in the composition. In particular embodiments, the amount of tetrahydrofarnesene is from about 16 wt. % to about 14 wt. %. In particular embodiments, the amount of tetrahydrofarnesene is from about 16 wt. % to about 14 wt. %, compared to the total amount of farnesene and farnesene derivatives in the composition. In particular embodiments, the amount of tetrahydrofarnesene is from about 15 wt. % to about 14 wt. %. In particular embodiments, the amount of tetrahydrofarnesene is from about 15 wt. % to about 14 wt. %, compared to the total amount of farnesene and farnesene derivatives in the composition. In particular embodiments, the amount of tetrahydrofarnesene is from about 20 wt. % to about 2 wt. %. In particular embodiments, the amount of tetrahydrofarnesene is from about 20 wt. % to about 2 wt. %, compared to the total amount of farnesene and farnesene derivatives in the composition. In particular embodiments, the amount of tetrahydrofarnesene is from about 16 wt. % to about 2 wt. %. In particular embodiments, the amount of tetrahydrofarnesene is from about 16 wt. % to about 2 wt. %, compared to the total amount of farnesene and farnesene derivatives in the composition. In particular embodiments, the amount of tetrahydrofarnesene is about 3 wt. %. In particular embodiments, the amount of tetrahydrofarnesene is about 3 wt. %, compared to the total amount of farnesene and farnesene derivatives in the composition. Those of skill will recognize that the amount of tetrahydrofarnesene is selected so that the total of dihydrofarnesene and tetrahydrofarnesene is less than or equal to 100%.

In certain embodiments, the compositions comprise a high amount of dihydrofarnesene and tetrahydrofarnesene together. In useful embodiments, the total amount of dihydrofarnesene and tetrahydrofarnesene is sufficient to give the composition a desired solvency. In particular embodiments, the total amount of dihydrofarnesene and tetrahydrofarnesene is from about 60 wt. % to about 100 wt. %. In particular embodiments, the total amount of dihydrofarnesene and tetrahydrofarnesene is from about 60 wt. % to about 100 wt. %, compared to the total amount of farnesene and farnesene derivatives in the composition. In particular embodiments, the total amount of dihydrofarnesene and tetrahydrofarnesene is from about 65 wt. % to about 100 wt. %. In particular embodiments, the total amount of dihydrofarnesene and tetrahydrofarnesene is from about 65 wt. % to about 100 wt. %, compared to the total amount of farnesene and farnesene derivatives in the composition. In particular embodiments, the total amount of dihydrofarnesene and tetrahydrofarnesene is from about 70 wt. % to about 100 wt. %. In particular embodiments, the total amount of dihydrofarnesene and tetrahydrofarnesene is from about 70 wt. % to about 100 wt. %, compared to the total amount of farnesene and farnesene derivatives in the composition. In particular embodiments, the total amount of dihydrofarnesene and tetrahydrofarnesene is from about 75 wt. % to about 100 wt. %. In particular embodiments, the total amount of dihydrofarnesene and tetrahydrofarnesene is from about 75 wt. % to about 100 wt. %, compared to the total amount of farnesene and farnesene derivatives in the composition. In particular embodiments, the total amount of dihydrofarnesene and tetrahydrofarnesene is from about 75 wt. % to about 90 wt. %. In particular embodiments, the total amount of dihydrofarnesene and tetrahydrofarnesene is from about 75 wt. % to about 90 wt. %, compared to the total amount of farnesene and farnesene derivatives in the composition. In particular embodiments, the total amount of dihydrofarnesene and tetrahydrofarnesene is from about 77 wt. % to about 87 wt. %. In particular embodiments, the total amount of dihydrofarnesene and tetrahydrofarnesene is from about 77 wt. % to about 87 wt. %, compared to the total amount of farnesene and farnesene derivatives in the composition. In particular embodiments, the total amount of dihydrofarnesene and tetrahydrofarnesene is from about 78 wt. % to about 85 wt. %. In particular embodiments, the total amount of dihydrofarnesene and tetrahydrofarnesene is from about 78 wt. % to about 85 wt. %, compared to the total amount of farnesene and farnesene derivatives in the composition. In particular embodiments, the total amount of dihydrofarnesene and tetrahydrofarnesene is from about 79 wt. % to about 85 wt. %. In particular embodiments, the total amount of dihydrofarnesene and tetrahydrofarnesene is from about 79 wt. % to about 85 wt. %, compared to the total amount of farnesene and farnesene derivatives in the composition. In particular embodiments, the total amount of dihydrofarnesene and tetrahydrofarnesene is from about 80 wt. % to about 85 wt. %. In particular embodiments, the total amount of dihydrofarnesene and tetrahydrofarnesene is from about 80 wt. % to about 85 wt. %, compared to the total amount of farnesene and farnesene derivatives in the composition. In particular embodiments, the total amount of dihydrofarnesene and tetrahydrofarnesene is from about 81 wt. % to about 85 wt. %. In particular embodiments, the total amount of dihydrofarnesene and tetrahydrofarnesene is from about 81 wt. % to about 85 wt. %, compared to the total amount of farnesene and farnesene derivatives in the composition. In particular embodiments, the total amount of dihydrofarnesene and tetrahydrofarnesene is from about 82 wt. % to about 85 wt. %. In particular embodiments, the total amount of dihydrofarnesene and tetrahydrofarnesene is from about 82 wt. % to about 85 wt. %, compared to the total amount of farnesene and farnesene derivatives in the composition. In particular embodiments, the total amount of dihydrofarnesene and tetrahydrofarnesene is from about 83 wt. % to about 85 wt. %. In particular embodiments, the total amount of dihydrofarnesene and tetrahydrofarnesene is from about 83 wt. % to about 85 wt. %, compared to the total amount of farnesene and farnesene derivatives in the composition. In particular embodiments, the total amount of dihydrofarnesene and tetrahydrofarnesene is from about 84 wt. % to about 85 wt. %. In particular embodiments, the total amount of dihydrofarnesene and tetrahydrofarnesene is from about 84 wt. % to about 85 wt. %, compared to the total amount of farnesene and farnesene derivatives in the composition. In particular embodiments, the total amount of dihydrofarnesene and tetrahydrofarnesene is from about 97 wt. % to about 100 wt. %. In particular embodiments, the total amount of dihydrofarnesene and tetrahydrofarnesene is from about 97 wt. % to about 100 wt. %, compared to the total amount of farnesene and farnesene derivatives in the composition. In particular embodiments, the total amount of dihydrofarnesene and tetrahydrofarnesene is from about 98 wt. % to about 100 wt. %. In particular embodiments, the total amount of dihydrofarnesene and tetrahydrofarnesene is from about 98 wt. % to about 100 wt. %, compared to the total amount of farnesene and farnesene derivatives in the composition. In particular embodiments, the total amount of dihydrofarnesene and tetrahydrofarnesene is from about 99.0 wt. % to about 99.7 wt. %. In particular embodiments, the total amount of dihydrofarnesene and tetrahydrofarnesene is from about 99.0 wt. % to about 99.7 wt. %, compared to the total amount of farnesene and farnesene derivatives in the composition.

The compositions can further comprise hexahydrofarnesene. In particular embodiments, the amount of hexahydrofarnesene is from about 0.1 wt. % to about 2 wt. % of the composition. In particular embodiments, the amount of hexahydrofarnesene is from about 0.1 wt. % to about 2 wt. %, compared to the total amount of farnesene and farnesene derivatives in the composition. In particular embodiments, the amount of hexahydrofarnesene is from about 0.1 wt. % to about 1.75 wt. % of the composition. In particular embodiments, the amount of hexahydrofarnesene is from about 0.1 wt. % to about 1.75 wt. %, compared to the total amount of farnesene and farnesene derivatives in the composition. In particular embodiments, the amount of hexahydrofarnesene is from about 0.1 wt. % to about 1.5 wt. % of the composition. In particular embodiments, the amount of hexahydrofarnesene is from about 0.1 wt. % to about 1.5 wt. %, compared to the total amount of farnesene and farnesene derivatives in the composition. In particular embodiments, the amount of hexahydrofarnesene is from about 0.1 wt. % to about 1.25 wt. % of the composition. In particular embodiments, the amount of hexahydrofarnesene is from about 0.1 wt. % to about 1.25 wt. %, compared to the total amount of farnesene and farnesene derivatives in the composition. In particular embodiments, the amount of hexahydrofarnesene is from about 0.1 wt. % to about 1.0 wt. % of the composition. In particular embodiments, the amount of hexahydrofarnesene is from about 0.1 wt. % to about 1.0 wt. %, compared to the total amount of farnesene and farnesene derivatives in the composition. In particular embodiments, the amount of hexahydrofarnesene is from about 0.1 wt. % to about 0.75 wt. % of the composition. In particular embodiments, the amount of hexahydrofarnesene is from about 0.1 wt. % to about 0.75 wt. %, compared to the total amount of farnesene and farnesene derivatives in the composition. In particular embodiments, the amount of hexahydrofarnesene is from about 0.1 wt. % to about 0.5 wt. % of the composition. In particular embodiments, the amount of hexahydrofarnesene is from about 0.1 wt. % to about 0.5 wt. %, compared to the total amount of farnesene and farnesene derivatives in the composition. In particular embodiments, the amount of hexahydrofarnesene is from about 0.1 wt. % to about 0.4 wt. % of the composition. In particular embodiments, the amount of hexahydrofarnesene is from about 0.1 wt. % to about 0.4 wt. %, compared to the total amount of farnesene and farnesene derivatives in the composition. In particular embodiments, the amount of hexahydrofarnesene is from about 0.1 wt. % to about 0.3 wt. % of the composition. In particular embodiments, the amount of hexahydrofarnesene is from about 0.1 wt. % to about 0.3 wt. %, compared to the total amount of farnesene and farnesene derivatives in the composition. In particular embodiments, the amount of hexahydrofarnesene is about 0 wt. % of the composition (not detected by detection methods described herein), and thus substantially free of hexahydrofarnesene. In particular embodiments, the amount of hexahydrofarnesene is about 0 wt. %, compared to the total amount of farnesene and farnesene derivatives in the composition. Those of skill will recognize that the amount of hexahydrofarnesene is selected so that the total amount of dihydrofarnesene, tetrahydrofarnesene and hexahydrofarnesene is less than or equal to about 100%.

The hexahydrofarnesene can be analogous to or derived from α-farnesene or β-farnesene, where the distinction is appropriate. In certain embodiments, the farnesene is β-farnesene, again where the distinction is appropriate. In the hexahydrofarnesenes, any three double bonds can be hydrogenated. In particular embodiments, at least the α-double bond is hydrogenated. In the farnesene structures above, the α-double bond is depicted at the right side of the molecule.

The compositions can further comprise farnesane. In preferred embodiments, the farnesane is present in a small amount. In particular embodiments, the amount of farnesane is from about 0 wt. % to about 10 wt. % of the composition. In particular embodiments, the amount of farnesane is from about 0 wt. % to about 10 wt. %, compared to the total amount of farnesene and farnesene derivatives in the composition. In particular embodiments, the amount of farnesane is from about 0 wt. % to about 7.5 wt. % of the composition. In particular embodiments, the amount of farnesane is from about 0 wt. % to about 7.5 wt. %, compared to the total amount of farnesene and farnesene derivatives in the composition. In particular embodiments, the amount of farnesane is from about 0 wt. % to about 5 wt. % of the composition. In particular embodiments, the amount of farnesane is from about 0 wt. % to about 5 wt. %, compared to the total amount of farnesene and farnesene derivatives in the composition. In particular embodiments, the amount of farnesane is from about 0 wt. % to about 2.5 wt. % of the composition. In particular embodiments, the amount of farnesane is from about 0 wt. % to about 2.5 wt. %, compared to the total amount of farnesene and farnesene derivatives in the composition. In particular embodiments, the amount of farnesane is from about 0 wt. % to about 2 wt. % of the composition. In particular embodiments, the amount of farnesane is from about 0 wt. % to about 2 wt. %, compared to the total amount of farnesene and farnesene derivatives in the composition. In particular embodiments, the amount of farnesane is from about 0 wt. % to about 1 wt. % of the composition. In particular embodiments, the amount of farnesane is from about 0 wt. % to about 1 wt. %, compared to the total amount of farnesene and farnesene derivatives in the composition. In particular embodiments, the amount of farnesane is from about 0 wt. % to about 0.5 wt. % of the composition. In particular embodiments, the amount of farnesane is from about 0 wt. % to about 0.5 wt. %, compared to the total amount of farnesene and farnesene derivatives in the composition. In particular embodiments, the amount of farnesane is from about 0 wt. % to about 0.2 wt. % of the composition. In particular embodiments, the amount of farnesane is from about 0 wt. % to about 0.2 wt. %, compared to the total amount of farnesene and farnesene derivatives in the composition. In particular embodiments, the amount of farnesane is from about 0 wt. % to about 0.1 wt. % of the composition. In particular embodiments, the amount of farnesane is from about 0 wt. % to about 0.1 wt. %, compared to the total amount of farnesene and farnesene derivatives in the composition. In particular embodiments, the compositions are substantially free of farnesane.

The compositions can further comprise bisabolene/farnesene. In preferred embodiments, the amount of bisabolene/farnesene is at a small amount. In particular embodiments, the amount of bisabolene/farnesene is from 0 wt. % to 0.5 wt. % of the composition. In particular embodiments, the amount of bisabolene/farnesene is from 0 wt. % to 0.5 wt. %, compared to the total amount of farnesene and farnesene derivatives in the composition. In particular embodiments, the amount of bisabolene/farnesene is from 0 wt. % to 0.4 wt. % of the composition. In particular embodiments, the amount of bisabolene/farnesene is from 0 wt. % to 0.4 wt. %, compared to the total amount of farnesene and farnesene derivatives in the composition. In particular embodiments, the amount of bisabolene/farnesene is from 0 wt. % to 0.3 wt. % of the composition. In particular embodiments, the amount of bisabolene/farnesene is from 0 wt. % to 0.3 wt. %, compared to the total amount of farnesene and farnesene derivatives in the composition. In particular embodiments, the amount of bisabolene/farnesene is from 0 wt. % to 0.2 wt. % of the composition. In particular embodiments, the amount of bisabolene/farnesene is from 0 wt. % to 0.2 wt. %, compared to the total amount of farnesene and farnesene derivatives in the composition. In particular embodiments, the amount of bisabolene/farnesene is from 0 wt. % to 0.1 wt. % of the composition. In particular embodiments, the amount of bisabolene/farnesene is from 0 wt. % to 0.1 wt. %, compared to the total amount of farnesene and farnesene derivatives in the composition. In particular embodiments, the compositions are substantially free of bisabolene/farnesene.

In the above embodiments, the wt. % is measured by any technique apparent to those of skill in the art. In particular embodiments, the wt. % is measured by mass spectrometry, by gas chromatography-mass spectrometry (GC-MS) or by gas chromatography-flame ionization detection (GC-FID). In some embodiments, the wt. % is that of the entire composition. In some embodiments, the wt. % is relative to the total amount of farnesene and farnesene derivatives in the composition. The farnesene derivatives include dihydrofarnesene, tetrahydrofarnesene, hexahydrofarnesene, farnesane, and multimers of these (including homomultimers and heteromultimers), as well as multimers of farnesene. In preferred embodiments, the compositions comprise less than 0.5 wt. % multimers. The compositions can include further reactive derivatives of farnesene and/or farnesane. These include oxidative derivatives, hydroxyl derivatives such as farnesol, epoxy derivatives, and other derivatives of farnesene and/or farnesane recognized by those of skill in the art. In preferred embodiments, these reactive derivatives make up less than 1.5 wt. % of the composition.

In certain embodiments, the farnesene and farnesene derivatives comprise, on average, about 1.0 to about 1.4 double bonds per molecule of farnesene and farnesene derivative in the composition. In other words, the ratio of the total number of double bonds of farnesene and farnesene derivative molecules in the composition versus the total number of farnesene and farnesene derivative molecules in the composition is about 1.0 to about 1.4. In certain embodiments, the farnesene and farnesene derivatives comprise, on average, about 1.0 to about 1.3 double bonds per molecule of farnesene and farnesene derivative in the composition. In certain embodiments, the farnesene and farnesene derivatives comprise, on average, about 1.0 to about 1.2 double bonds per molecule of farnesene and farnesene derivative in the composition. In certain embodiments, the farnesene and farnesene derivatives comprise, on average, about 1.04 to about 1.16 double bonds per molecule of farnesene and farnesene derivative in the composition.

Advantageously, in certain embodiments, the compositions provide extended oxidative stability. In certain embodiments, provided are compositions described herein with greater than 99% oxidative stability at least 100 weeks at 25° C. In further embodiments, the compositions provide extended pH stability. In certain embodiments, provided are compositions described herein with greater than 99% pH stability at pH 4 over 30 minutes at 25° C. In certain embodiments, provided are compositions described herein with greater than 99% pH stability at pH 1 over 30 minutes at 25° C. In certain embodiments, provided are compositions described herein with greater than 99% pH stability at pH 13 over 30 minutes at 25° C. In certain embodiments, provided are compositions described herein having Hansen solubility parameters of δH equal to about 2.0 and δP equal to about 1.0.

Preparation of Compositions

The compositions provided herein can be prepared, isolated or obtained by any method apparent to those of skill in the art. Useful methods of preparing farnesene are described in U.S. Pat. Nos. 7,659,097 B2, 7,399,323 B2, 7,846,222 B2, 8,257,957 B2 or International Patent Publication No. WO 2007/139924 A2, each of which is incorporated herein by reference in its entirety. Useful methods for partially hydrogenating farnesene are described in U.S. Pat. No. 8,519,204 B2 and in International Pat. Publ. No. WO 2012/141784 A1, each of which is incorporated herein by reference in its entirety. Other methods for partially hydrogenating farnesene will be apparent to those of skill in the art.

In some embodiments, the methods comprise reacting a controlled amount of hydrogen with farnesene in the presence of a catalyst under controlled reaction conditions to produce the partially hydrogenated farnesene such as β-farnesene. The controlled amount of hydrogen corresponds to a molar equivalent of desired degree of hydrogenation in the olefin. For example, to make a 75% hydrogenated olefin from farnesene, the controlled amount of hydrogen would be about 3 molar equivalents of hydrogen. In another example, to make a 25% hydrogenated olefin from farnesene, the controlled amount of hydrogen would be about 1 molar equivalent of hydrogen. In some embodiments, at least some of the farnesene is produced by a bioengineered microorganism using a renewable carbon source. In some embodiments, plurality of the farnesene is produced by a bioengineered microorganism using a renewable carbon source. In some embodiments, a majority of the farnesene is produced by a bioengineered microorganism using a renewable carbon source.

The distribution of species (e.g., dihydrofarnesene, tetrahydrofarnesene, hexahydrofarnesene, farnesene, and farnesane) produced by partial hydrogenation can be controlled through selecting the type, activity and loading of the catalyst, the catalyst conditions (e.g., temperature, pressure, time of reaction, controlled hydrogen delivery), and starting material (e.g., impurities in farnesene). By controlling these parameters, a composition comprising various proportions of dihydrofarnesene and tetrahydrofarnesene, compared to total farnesene/farnesane (e.g., the total amount of farnesene and farnesene derivatives), can be produced.

For the methods described herein, any suitable hydrogenation catalyst may be used. For example, in some variations, a catalyst is selected from the group consisting of Pd, Pt, Ni, Ru, Ir, Cu, Fe, Raney-type porous catalysts such as Ni/Al, Co/Al and Cu/Al, alloys of platinum group catalysts with promoters or stabilizers such as Mo, Co, Mg and Zn, and hydroprocessing catalysts such as NiMoS and CoMoS. Exemplary catalysts are described in U.S. Pat. Nos. 6,403,844 B1; 5,378,767 A; 5,151,172 A; and 3,702,348 A, each of which is incorporated herein by reference in its entirety. In some variations, the catalyst is or comprises Pd/C, e.g., 5 wt. % Pd/C or 10 wt. % Pd/C. In some variations, the catalyst is or comprises $Pd/Al_2O_3$, e.g., 0.3 wt. % $Pd/Al_2O_3$. In some variations, the catalyst is or comprises a Lindlar catalyst, e.g., Pd on calcium carbonate or barium carbonate and treated with lead (e.g., lead oxide or lead acetate). For example, a Lindlar catalyst comprising $Pd/Pb/BaCO_3$ may be used. In some variations, the catalyst is or comprises Ni, e.g., Raney Ni, sponge nickel, or skeletal nickel. In some variations, a nickel catalyst is used that is supported by $Al_2O_3$, e.g., about 20%, 12% or 8% $Ni/Al_2O_3$. In some variations the catalyst comprises nickel sulfide. In some variations, the catalyst comprises molybdenum sulfide, e.g., molybdenum sulfide catalysts having a ratio of sulfur to molybdenum of two-to-one, e.g., $MoS_2$, supported on alumina, e.g., activated alumina having a surface area of about 300 square meters per gram or more, or silica gel, activated charcoal, acid treated clay, silica-alumina complexes, e.g., as disclosed in U.S. Pat. No. 2,674,632 A which is incorporated by reference herein in its entirety.

The catalyst can be provided in any suitable form, e.g., with a minimum dimension of at least about 1 mm. Particle dimensions may be selected depending on catalyst type and catalysis conditions (e.g., slurry batch, fixed bed, fluidized bed, or continuous flow reactor). The catalyst may be selected to have a specified surface area to produce the desired distribution of partially hydrogenated hydrocarbon terpene species, such as the farnesene molecules described herein, and may be formed in any suitable form factor, e.g., cylinders, tablets, granules, spheres, lobed cylinders, and the like. In certain variations, the catalyst contains voids, e.g., in the form of channels, passages, or holes. In some variations, the catalyst comprises an extrudate, e.g., an extrude having a desired cross-sectional shape, such as a lobed extrude (e.g. trilobe extrudate). In some variations, the catalyst is or comprises $Pd/Al_2O_3$, e.g., 0.3 wt. % $Pd/Al_2O_3$ tribobe extrudate.

The catalyst can be used with a support. Any suitable support can be used, e.g., carbon, silica, titania, zirconia, alumina, kieselguhr, magnesia, calcium aluminate cements, and other inorganic materials. In some cases, supports are activated. Modified versions of such supports can be used, e.g., base-treated supports or supports treated with stabilizing additives such as MgO. A support can have any suitable form factor (e.g., a pellet or extrudate) with dimensions on the order of about 0.1-5 mm, 0.5-5 mm, 1-5 mm, 1-4 mm, or 1-3 mm.

The hydrogenation catalyst may be used in any effective loading. In some variations (e.g., for 5 wt. % Pd/C or 10 wt. % Pd/C), an effective catalyst loading will be 1/1000, 2/1000, 3/1000, 4/1000, or 5/1000. For example, in some variations β-farnesene can be partially hydrogenated using 5 wt. % Pd/C at a loading of 1/1000, 2/1000, 3/1000, 4/1000, or 5/1000.

During the partial hydrogenation process, it is desired to deliver a controlled amount of hydrogen under controlled reaction conditions so as to control the extent of and site selectivity of the hydrogenation. Such controlled hydrogenation can be accomplished in a variety of ways, and using a variety of equipment configurations. For example, continuous hydrogen uptake by the sample may be controlled and/or measured using a flow meter, flow totalizer, or the like, or hydrogen may be delivered to the sample in discrete or quantized molar aliquots, e.g., discrete aliquots of 0.25, 0.5, or 1 mol $H_2$ per mol farnesene. In some variations, a batch slurry hydrogenation reactor is used. In some variations, a fixed bed reactor is used for partial hydrogenation. In some variations, a fluidized bed reactor is used for partial hydrogenation.

The temperature of the hydrogenation may be selected to control the rate of reaction, which may, in some situations, enhance site selectivity of the hydrogenation. In certain variations, a suitable hydrogenation temperature is in a range from about 50° C. to about 150° C., e.g., about 50° C., 60° C., 70° C., 80° C., 90° C., 100° C., 110° C., 120° C., 130° C., 140° C., or 150° C. In some variations, the reaction is conducted at about 80° C. In some variations, the reaction is conducted at about 100° C. In some variations, the reaction is at least partially self-heated during early stages when the exothermic reaction is generating sufficient heat, and external heat is added during latter stages. In some variations, the reactor is cooled to keep the temperature of the exothermic hydrogenation process at or below a selected hydrogenation temperature.

The hydrogen pressure used may be in a range from about 50 psig-1000 psig, e.g., about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 psig.

One method for partially hydrogenating farnesene comprises immersing a catalyst into liquid farnesene to form a slurry and delivering a controlled amount of hydrogen to the slurry in a closed reactor, where the controlled amount of hydrogen corresponds to a molar equivalent of desired hydrogenation degree. The method comprises hydrogenating the farnesene at a temperature between about 50° C. and 150° C. until the controlled amount of hydrogen is substantially consumed, and removing the catalyst from the hydrogenated farnesene. For example, in the case of β-farnesene, one molar equivalent of hydrogen delivered to the slurry in the closed reactor corresponds to 25% hydrogenation, two molar equivalents of hydrogen delivered to the slurry in the closed reactor corresponds to 50% hydrogenation, and three molar equivalents corresponds to 75% hydrogenation. The controlled amount of hydrogen may be delivered to the slurry in one or more discrete aliquots or as a continuous stream.

In one variation, molar equivalents of hydrogen are delivered to the slurry (e.g., 5 wt. % Pd/C (palladium on carbon) at a loading of about 1-5 g/kg hydrocarbon farnesene or about 3-5 g/kg farnesene) in the closed reactor in discrete aliquots, e.g., each aliquot corresponding to about 0.5 mol $H_2$ per mol hydrocarbon farnesene in the reactor, at a pressure of 50-1000 psig. After each aliquot (or pair of aliquots) is delivered to the reactor, the hydrogenation reaction is allowed to proceed until the hydrogen is substantially consumed. If more extensive hydrogenation is desired, another aliquot (or pair of aliquots) is delivered to the reactor and allowed to proceed until the hydrogen is substantially consumed, and so forth. Following the reaction, the catalyst can be removed from the partially hydrogenated farnesene using known techniques.

In another variation, the method of partially hydrogenating farnesene comprises immersing a 5% Pd/C catalyst into liquid farnesene at 0.025-0.1% (w/w) to form a slurry and delivering a controlled amount of hydrogen to the slurry in a closed reactor, where the controlled amount of hydrogen corresponds to a molar equivalent of desired hydrogenation degree as described above. In one embodiment, to minimize polymer formation during the initial phase of the hydrogenation, the reaction can be run at between about 100-120° C. and at about 75-150 psig $H_2$ until the controlled amount of hydrogen is substantially consumed. The controlled amount of hydrogen may be delivered to the slurry in one or more discrete aliquots or as a continuous stream. The catalyst can then be removed from the hydrogenated farnesene using known techniques.

In certain embodiments, the present compositions can be filtered to remove odor and residual anti-oxidant stabilizers (e.g., 4-tert-butylcatechol, also referred to as "TBC") which may be present in the feedstock. In an embodiment, a method of producing the present compositions can comprise contacting the partially hydrogenated farnesene composition, produced by hydrogenating farnesene, with a solid adsorbent, such as alumina and/or silica. In another embodiment, the starting material (i.e., a composition comprising farnesene) can be filtered to remove organic acids and other oxygenates before contacting the starting material with a hydrogenation catalyst to make the hydrogenation process more efficient. In some embodiments, the present compositions can be treated using adsorbents both before and after the hydrogenation process.

The adsorbent filtering process can be performed using any suitable methods. For example, a column process can be used where the adsorbent is heated in the presence or absence of a vacuum. The heating process drives residual water off of the solid adsorbent and provides an activated version of the adsorbent (i.e., greater degree of adsorption active sites). After cooling the adsorbent, the farnesene or partially hydrogenated farnesene compositions can be passed through the column, thereby producing a material with diminished odor and no detectable levels of TBC. In another example, the farnesene or partially hydrogenated farnesene compositions can be added to about 0.5 to about 5% (w/w) unactivated solid adsorbents and agitated in a batch reactor for a period of about 1 to 12 hours. After removing small, volatile, organic oxygenate compounds, the post-treated partially hydrogenated farnesene compositions generally exhibit a diminished odor and no detectable levels of TBC.

In certain embodiments, the compositions disclosed herein are free or substantially free of small, volatile, organic oxygenate compounds (e.g., alcohols, acids, aldehydes, 6-methyl-5-penten-2-one, or the like) which can cause an odor in the composition. These impurities are typically $C_4$ to $C_{10}$ compounds. The $C_4$ to $C_{10}$ volatile, organic oxygenate compounds are generally detected at early retention times in the GC chromatograph prior to filtering with adsorbents. These oxygenate compounds are typically detected in an amount (wt. % or % area) between about 0.01 wt. % to about 0.1 wt. % (e.g., 0.031% area) based on the total weight of the composition. However, after filtering the partially hydrogenated farnesene composition with adsorbents, these oxygenate compounds are generally not detected in the GC chromatography (e.g., 0.0% area).

In certain embodiments, the compositions disclosed herein are free or substantially free of TBC. In some embodiments, TBC is detectable by GC or liquid chromatography (e.g., greater than 0.01 ppm, 0.1 ppm, 1 ppm, or the like) but at a concentration of 10 ppm or less. The presence of TBC in a larger amount (e.g., 40 ppm or more) in end products comprising water, alcohol, or other components can impart color (e.g., blue in water and pink in alcohol), which may not be desirable in some applications. In certain embodiments, TBC is filtered and removed together with other small, volatile, organic oxygenates from the compositions disclosed herein.

In certain embodiments, after adsorbent filtering process, a stabilizer may be added as an anti-oxidant to stabilize the partially hydrogenated compositions described herein. Any suitable stabilizers include those, which, when oxidized, do not change color of the composition. In some embodiments, suitable stabilizers, which, when oxidized, do not form a quinone. A stabilizer, such as a hydroquinone, can react with water, alcohol, or other ingredients in a composition and impart visible color, which is generally not desirable in end products. In particular embodiments, butylated hydroxytoluene (BHT) may be used as a stabilizer.

Any suitable amount of stabilizer may be added to the present compositions. In some embodiments, a stabilizer may be present in the partially hydrogenated farnesene compositions at a concentration between about 10 ppm to about 1,000 ppm, typically about 100 ppm to about 500 ppm, more typically about 100 ppm. In some embodiments, end products (e.g., solvent, cleaning products, degreaser, personal care products) generally comprise a stabilizer at a concentration of about 100 ppm or less.

Methods of Use and Mixtures

In certain embodiments, provided herein are methods of using the compositions and composition mixtures. Due to their advantageous solvencies, the compositions provided herein are useful as various consumer and industrial products such as solvents, cleaning products, degreasers, metal cleaners, personal care products, and for other end uses. The compositions can be used in any method deemed suitable by the practitioner of skill. In certain embodiments, provided are methods of cleaning. The methods comprise the step of contacting a substrate with a sufficient amount of a composition and/or a product provided herein to clean the substrate. In certain embodiments, provided are methods of degreasing. The methods comprise the step of contacting a substrate with a sufficient amount of a composition and/or a product provided herein to degrease the substrate. Useful substrates include, but are not limited to, domestic and commercial surfaces, skin, hands, floors, walls, engines, clothing, ovens, automobiles, automobile interiors, metals, metal parts, and any other substrate deemed suitable by the practitioner of skill.

In certain embodiments, provided are methods of treating or conditioning skin, hair, or nails. The methods comprise the step of applying to the skin, hair, nails, or any other suitable substrates with a sufficient amount of a composition and/or a product provided herein to enhance appearance and/or other properties of the skin, hair, or nails.

In certain embodiments, the compositions are useful in the methods described herein on their own. In other embodiments, the compositions can be mixed with one or more additional components to make a solvent, a degreaser, a general cleaning product, a metal cleaning product, a personal care product, and the like. In certain embodiments, the compositions are mixed with one or more co-solvents or surfactants, or both. In certain embodiments, the compositions are mixed with at least one additional component, such as a co-solvent, surfactant, water, emulsifier, emollient, thickener, or a mixture thereof.

In certain embodiments, the compositions can further comprise additives known to the practitioner of skill in the art. Useful additives include, but are not limited to, delaminates, buffering agents, pH control agents, fragrances, perfumes, flavors, defoamers, dyes, whiteners, brighteners, solubilizing materials, stabilizers, thickeners, corrosion inhibitors, lotions, mineral oils, enzymes, cloud point modifiers, preservatives, ion exchangers, chelating agents, sudsing control agents, soil removal agents, softening agents, opacifiers, inert diluents, graying inhibitors, stabilizers, polymers, abrasive, exfoliant, and the like, and combinations thereof.

In certain embodiments, one or more additional components/additives can be added to the present compositions or end products to enhance their properties or functions. As used herein, the term additional component/additive does not include reactants or reaction products produced by hydrogenation of farnesene, such as farnesene, dihydrofarnesene, tetrahydrofarnesene, hexahydrofarnesene, farnesane, and multimers of these (including homomultimers and heteromultimers). While these reactants or reaction products may be present in the compositions as a result of hydrogenation of farnesene, one or more additional components/additives refer to components/additives deliberately added to the partially hydrogenated farnesene compositions for functional purposes. As used herein, the terms "component" and "additive" are used interchangeably, and the same ingredient, e.g., a limonene, may be referred to as a component (e.g., co-solvent) or an additive (e.g., fragrance) depending on its purpose and/or amount in the composition.

Useful co-solvents that can be added to the present compositions include, but are not limited to, saturated hydrocarbon solvents, glycol ethers, fatty acid methyl esters, aliphatic hydrocarbon solvents, acyclic hydrocarbon solvents, halogenated solvents, aromatic hydrocarbon solvents, cyclic terpenes, unsaturated hydrocarbon solvents, halocarbon solvents, polyols, ethers, glycol esters, alcohols, ketones, and any combination thereof. In an embodiment, a composition provided herein further comprises a co-solvent selected from the group consisting of limonene, benzene, toluene, xylene, aromatic high flash aromatic naptha (e.g., aromatic 200), soy methyl ester, ethyl lactate, paraffins (e.g., isopar M), dibasic esters (e.g., DBE-LVP), paraffinic naphthenic solvent, propylene glycol, ethyl alcohol, and mixtures thereof. The addition of such a co-solvent can cause the solvent blend-to-surfactant ratio in the composition to increase.

Useful surfactants that can be added to the present compositions include, but are not limited to, nonionic surfactants, cationic surfactants, anionic surfactants, amphoteric surfactants, zwitterionic surfactants, or a mixture thereof. Examples of nonionic surfactants include, but are not limited to, one or more of amides such as alkanolamides, ethoxylated alkanolamides, ethylene bisamides; esters such as fatty acid esters, glycerol esters, ethoxylated fatty acid esters, sorbitan esters, ethoxylated sorbitan; ethoxylates such as alkylphenol ethoxylates, alcohol ethoxylates, tristyrylphenol ethoxylates, mercaptan ethoxylates; end-capped and EO/PO block copolymers such as ethylene oxide/propylene oxide block copolymers, chlorine capped ethoxylates, tetra-functional block copolymers; amine oxides such lauramine oxide, cocamine oxide, stearamine oxide, stearamidopropylamine oxide, palmitamidopropylamine oxide, decylamine oxide; fatty alcohols such as decyl alcohol, lauryl alcohol, tridecyl alcohol, myristyl alcohol, cetyl alcohol, ethyl alcohol, stearyl alcohol, oleyl alcohol, linoleyl alcohol and linolenyl alcohol; and alkoxylated alcohols such as ethoxylated lauryl alcohol, trideceth alcohols; and fatty acids such as lauric acid, oleic acid, stearic acid, myristic acid, cetearic acid, isostearic acid, linoleic acid, linolenic acid, ricinoleic acid, elaidic acid, arichidonic acid, myristoleic acid and mixtures thereof. Other examples of non-ionic surfactants include a glycol such as polyethylene glycol (PEG), alkyl PEG esters, polypropylene glycol (PPG) and derivatives thereof. In one embodiment, the surfactant is an alcohol ethoxylate, an alkyl phenol ethoxylate or a terpene alkoxylate.

Examples of cationic surfactants include, but are not limited to, quaternary ammonium compounds, such as cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl distearyldimonium chloride, dicetyl dimonium chloride, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, dicetyl dimonium chloride and distearyldimonium chloride; isostearylaminopropalkonium chloride or olealkonium chloride; behentrimonium chloride; as well as mixtures thereof.

Examples of anionic surfactants include, but are not limited to, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, sulfosuccinates, isethionates, and taurates, as well as mixtures thereof. Commonly used anionic surfactants that are suitable as the anionic surfactant component of the composition of the present invention include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium-monoalkyl phosphates, sodium dialkyl phosphates, sodium lauroyl sarcosinate, lauroyl sarcosine, cocoyl sarcosine, ammonium cocyl sulfate, ammonium lauryl sulfate, sodium cocyl sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium lauryl sulfate, potassium cocyl sulfate, potassium lauryl sulfate, monoethanolamine cocyl sulfate, sodium tridecyl benzene sulfonate, and sodium dodecyl benzene sulfonate. Branched anionic surfactants are particularly preferred, such as sodium trideceth sulfate, sodium tridecyl sulfate, ammonium trideceth sulfate, ammonium tridecyl sulfate, and sodium trideceth carboxylate.

Examples of amphoteric surfactants include, but are not limited to, derivatives of aliphatic secondary and tertiary amines in which the aliphatic radical can be straight chain or branched and wherein one of the aliphatic substituents contains from about 8 to about 18 carbon atoms and one contains an anionic water solubilizing group. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl arnphoglycinates, and alkyl amphopropionates, as well as alkyl iminopropionates, alkyl iminodipropionates, and alkyl amphopropylsulfonates, such as for example, cocoamphoacetate cocoarnphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

Examples of zwitterionic surfactants include, but are not limited to, alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

In certain embodiments, a composition provided herein comprises surfactants such as sodium lauryl ether sulfate, ethoxylated alcohol surfactants (e.g., Tomadol 25-3, Tomadol 25-7), fatty acid diethanolamine (e.g., cocamide DEA), orange oil emulsifier (e.g., Videt ME-80), acrylate-based emulsion copolymer (e.g., Alcogum SL-70), polyoxyethers of lauryl alcohol (e.g., Laureth-7), linear isopropylamine dodecylbenzene sulfonate (e.g., Rhodocal IPAM), blended alcohol ethoxylate (e.g., Videt Q3), alkoxylated alcohol (e.g., Tergitol 15-S-7), sodium iminodipropionate (e.g., Amphoteric 400), nonionic alcohol ethoxylates (e.g., Ecosurf EH-6), a palm kernel alcohol ethoxylated and propoxylated surfactant (e.g., Ecosurf SA-7), sodium xylene sulfonate (e.g., Alkatrope SXS-40), or mixtures thereof.

Useful emulsifiers that can be added to the present compositions include, but are not limited to, polysaccharide ethers, polyglycosides, fatty acids, fatty alcohols, amine oxides, water-soluble cellulose derivatives, alkyl sulfonates, ethoxylated alkyl phenols, alkanaolamides, betaines, zwiterionics, carboxylated alcohols, carboxylic acids, ethoxylated alcohols, and derivatives thereof. In certain embodiments, a composition provided herein further comprises emulsifiers, such as lauryl alcohol (e.g., Laureth-7), fatty acid diethanolamine (e.g., cocamide DEA), ammonium methyl sulfate and fatty alcohol ethoxylate (e.g., Steposol DG), Tomadyne 100 surfactant, linear alcohol ($C_{12-15}$) ethoxylate, POE-7, POE-3, sodium branched dodecyl benzene sulfonate, or mixtures thereof.

Useful emollients that can be added to the present compositions include, but are not limited to, conventional lipids materials (e.g., fats, waxes), polar lipids (lipids that have been modified to be more water soluble), silicones, hydrocarbons, and other solvent materials. Emollients can include, for example, petroleum based, fatty acid type, alkyl ethoxylate type, fatty acid ester ethoxylates, fatty alcohol type, polysiloxane type, mucopolysaccharides, or mixtures thereof. Other useful emollients also include polyhydric alcohols, e.g., glycerin and propylene glycol, and the like; polyols such as polyethylene glycols; saccharides and/or polysaccharides, such as sucrose, sorbitol; and urea derivatives such as hydroxyethyl urea and the like. In certain embodiments, a composition provided herein further comprises emollients, such as Crodamol STS (e.g., PPG-3 benzyl ether myristate), Versagel ME-750 (e.g., hydrogenated polyisobutene, butyelen/ethylene/styrene copolymer, ethylene/propylene/styrene copolymer), Softisan 649 (e.g., bis-diglyceryl polyacyladipate-2, Crodamol PTIS (pentaerythrityl tetraisosterate), Super Sterol Ester (e.g., $C_{10-30}$ cholesterol/lanosterol esters), or mixtures thereof.

Useful thickeners that can be added to the present compositions include, but are not limited to, organic thickeners and inorganic thickeners. Organic thickeners may include cellulosic thickeners and their derivatives, natural gums, acrylates, starches, stearates, and fatty acid alcohols. Inorganic thickeners may include clays and salts. Examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Examples of acrylates include potassium aluminum polyacrylate, sodium acrylate/vinyl alcohol copolymer, sodium polymethacrylate, and the like. Examples of starches include oat flour, potato starch, wheat flour, wheat starch, and the like. Examples of stearates include methoxy PEG-22/dodecyl glycol copolymer, PEG-2M, PEG-5M, and the like. Examples of fatty acid alcohols include caprylic alcohol, cetearyl alcohol, lauryl alcohol, oleyl alcohol, palm kernel alcohol, and the like. Some non-limiting examples of clays include bentonite, magnesium aluminum silicate, magnesium trisilicate, stearalkonium bentonite, trimethylamine magnesium aluminum silicate, and the like. Some non-limiting examples of salts include calcium chloride, sodium chloride, sodium sulfate, ammonium chloride, and the like. Some non-limiting examples of thickeners that may be used to thicken the non-aqueous portions of the composition include waxes such as candelilla wax, carnauba wax, beeswax, and the like, oils, vegetable oils and animal oils, and the like. In certain embodiments, the present compositions may further comprise thickeners, such as acrylates $C_{10-30}$ cross polymer, Kelzan ASX-T (e.g., xanthan gum), linear alcohol ethoxylate, $C_{12-14}$, or mixtures thereof.

Useful hydrotropes that can be added in the present compositions include, but are not limited to, sodium and ammonium xylene sulfonates, sodium alkyl disulfonates, solvents, particularly alcoholic solvents, such as ethanol, isopropanol, ethoxy diglycol, glycols and polyhydroxy compounds such as propylene glycol, methyl propane, diol, butylene glycol, hexylene glycol, glycerin, dextrose, sorbitol, sucrose, fructose, other sugars, or mixtures thereof.

Useful pH control agents and/or buffers that can be added to the present compositions include, but are not limited to, sodium hydroxide, potassium hydroxide, tetraethylammonium, sodium citrate, acetic acid, citric acid, hydrochloric acid, and the like. A pH control agent can be added in an amount as needed to keep the composition at a desired pH. Buffers, such as sodium metasilicate, pentahydrate, sodium bicarbonate can also be used to keep the composition at a desired pH. For example, a pH control agent may be added to keep the composition pH selected from about 1 to about 14 depending on the end use of the composition. For example, a composition for heavy duty industrial cleaning application can be formulated to have a pH of about 11 or about 13-14 with a pH control agent and/or buffer. Generally, a pH control agent and/or buffer is added in a small amount in the range of from about 0.1% to about 10%, typically in the range from about 0.5% to about 5%, based on the total weight of the composition.

Depending on end use or application, the present partially hydrogenated farnesene composition can be mixed at various proportions with one or more additional components or additives. In certain embodiments, the present partially hydrogenated farnesene composition may be added to a mixture as a major weight percent component, and at least one additional component/or additive may be added to the mixture as a minor weight percent component based on the total weight of the composition/product. For example, as shown in Example 17, a composition may comprise 69 wt. % of the present partially hydrogenated farnesene composition (e.g., Example 2 composition or any suitable partially hydrogenated farnesene compositions described herein) and 31 wt. % of at least one additional component (e.g., emulsifier and/or carrier). In certain embodiments, a composition/product comprises at least 50, 55, 60, 65, 70, 75, 80, 85, 90, 95, 96, 97, 98, or 99 wt. % of the present partially hydrogenated farnesene composition based on the total weight of the composition/product, and at least one additional component. In certain embodiments, a composition/product comprises the present partially hydrogenated farnesene composition as a minor weight percent component. For example, a composition/product comprises less than about 50, 45, 40, 35, 30, 25, 20, 15, 10, 5, 4, 3, 2, or 1 wt. % of the present partially hydrogenated farnesene composition and at least one additional component/additive. In certain embodiments, a composition/product comprises the present partially hydrogenated composition in any suitable range selected anywhere between about 0.1 wt. % to about 99.9 wt. %, typically between about 0.5 wt. % to about 99.9 wt. %, and at least one additional component/additive, based on the total weight of the composition.

In certain embodiments, a composition/product comprises a co-solvent as an additional component in the mixture with the present partially hydrogenated farnesene composition. In certain embodiments, a co-solvent can be included in the composition/product as a major weight percent component of the composition/product. For example, a composition/product can comprise at least about 50, 55, 60, 65, 70, 75, 80, 85, 90, 95, 96, 97, 98, or 99 wt. % of co-solvent and the present partially hydrogenated farnesene composition as a minor component. In other embodiments, a composition/product comprises a co-solvent as a minor component. For example, a composition/product comprises less than about 50, 45, 40, 35, 30, 25, 20, 15, 10, 5, 4, 3, 2, or 1 wt. % of a co-solvent and any suitable amount of the present partially hydrogenated farnesene composition. In certain embodiments, a composition/product comprises a co-solvent in any suitable range selected anywhere between about 0.1 wt. % to about 99.9 wt. %, typically between about 0.5 wt. % to about 99 wt. %, based on the total weight of the composition. The amount of co-solvent added to the composition/product depends on end use or application of the composition/product. For example, in making a solvent blend, the present partially hydrogenated farnesene composition and co-solvent(s) may be mixed at a ratio of about 70:30, 90:10, 75:25, or any suitable ratios as shown in the Examples section.

In certain embodiments, a composition/product comprises the present partially hydrogenated farnesene composition and a surfactant as an additional component. In certain embodiments, one or more surfactants are included in the composition/product as a major weight percent component. For example, as shown in Example 14, a composition/product can comprise one or more surfactants as a major component (e.g., 50 wt. %) of the total weight of the composition/product. In certain embodiments, a composition/product can comprise at least 50, 55, 60, 65, 70, 75, 80, 85, 90, 95, 96, 97, 98, or 99 wt. % of one or more surfactants as a major weight percent component and the present partially hydrogenated farnesene composition as a minor weight percent component based on the total weight of the composition/product. In other embodiments, one or more surfactants are included in the composition/production as a minor weight percent component as shown in Example 15. For example, a composition/product can comprise less than about 50, 45, 40, 35, 30, 25, 20, 15, 10, 5, 4, 3, 2, or 1 wt. % of surfactant and any suitable amount of the present partially hydrogenated farnesene composition. In certain embodiments, a composition/product comprises a surfactant in any suitable range selected anywhere between about 0.1 wt. % to about 99.9 wt. %, typically between about 0.5 wt. % to about 99 wt. %, based on the total weight of the composition. The amount of surfactant added to the composition/product depends on end use or application of the composition/product. For example, about 6 wt. % of the partially hydrogenated farnesene composition and about 3 wt. % of surfactant can be mixed with other components in making a hand cleaner as shown in Example 15.

In certain embodiments, a composition/product comprises water as at least one additional component in the mixture with the present partially hydrogenated farnesene composition. In certain embodiment, water can be included in the composition/product as a major weight percent component of the composition/product as a carrier or diluent. For example, as shown in Example 15, a composition/product can comprise water as a major component (e.g., 83.65 wt. % as a diluent), and the present partially hydrogenated farnesene composition (e.g., Example 2) as a solvent and as a minor component (e.g., 6.0 wt. %). In certain embodiments, a composition/product can comprise at least about 50, 55, 60, 65, 70, 75, 80, 85, 90, 95, 96, 97, 98, or 99 wt. % of water and the present partially hydrogenated farnesene composition as a minor component. In other embodiments, a composition/product comprises water as a minor component. For example, a composition/product can comprise less than about 50, 45, 40, 35, 30, 25, 20, 15, 10, 5, 4, 3, 2, or 1 wt. % of water and any suitable amount of the present partially hydrogenated farnesene composition. In certain embodiments, a composition/product comprises water in any suitable range selected anywhere between about 0.1 wt. % to about 99.9 wt. %, typically between about 0.5 wt. % to about 99 wt. %, based on the total weight of the composition. The amount of water added to the composition/product depends on end use or application of the composition/product. For example, for all purpose cleaner and engine degreaser, water may be added as a major component (e.g., at least 80 wt. % or at least 90 wt. %) and the present partially hydrogenated farnesene composition may be added as a minor weight percent component (e.g., less than 10 wt. % or about 1 wt. % or less). In another example, for all-purpose cleaner concentrate, both water and the present partially hydrogenated farnesene composition may be added as minor weight percent components (e.g., less than 10 wt. % for both as shown in Example 23).

In certain embodiments, a composition/product comprises the present partially hydrogenated farnesene composition and an emulsifier as an additional component. In certain embodiments, an emulsifier can be included in the composition/product as a major weight percent component of the composition/product. For example, a composition/product can comprise at least about 50, 55, 60, 65, 70, 75, 80, 85, 90, 95, 96, 97, 98, or 99 wt. % of emulsifier and the present partially hydrogenated farnesene composition as a minor component. In certain embodiments, one or more emulsifiers are included in the composition/product as a minor component. For example, a composition/product can comprise less than about 50, 45, 40, 35, 30, 25, 20, 15, 10, 5, 4, 3, 2, or 1 wt. % of emulsifier and any suitable amount of the present partially hydrogenated farnesene composition. In certain embodiments, a composition/product comprises one or more emulsifiers in any suitable range selected anywhere between about 0.1 wt. % to less than about 50 wt. %, typically between about 1 wt. % to less than about 50 wt. %, based on the total weight of the composition. The amount of emulsifier(s) added to the composition/product depends on end use or application of the composition/product. For example, about 69 wt. % of the partially hydrogenated farnesene composition and about 11 wt. % of emulsifier can be mixed with other components in making a solvent degreaser and ink remover as shown in Example 17.

In certain embodiments, a composition/product comprises the presently partially hydrogenated farnesene composition and an emollient as an additional component. In certain embodiments, an emollient can be included in the product as a major weight percent component of the composition/product. For example, a composition/product can comprise at least about 50, 55, 60, 65, 70, 75, 80, 85, 90, 95, 96, 97, 98, or 99 wt. % of emollient and the present partially hydrogenated farnesene composition as a minor component. In certain embodiments, one or more emollients are included in the composition/product as a minor component. For example, a composition/product can comprise less than about 50, 45, 40, 35, 30, 25, 20, 15, 10, 5, 4, 3, 2, or 1 wt.

% of emollient and any suitable amount of the present partially hydrogenated farnesene composition. In certain embodiments, a composition/product comprises one or more emollients in any suitable range selected anywhere between about 0.1 wt. % to less than about 50 wt. %, typically between about 1 wt. % to less than about 50 wt. %, based on the total weight of the composition. The amount of emollient(s) added to the composition/product depends on end use or application of the composition/product.

In certain embodiments, a composition/product comprises the presently partially hydrogenated farnesene composition and a thickener as an additional component. In certain embodiments, a thickener can be included in the product as a major weight percent component of the composition/product. For example, a composition/product can comprise at least about 50, 55, 60, 65, 70, 75, 80, 85, 90, 95, 96, 97, 98, or 99 wt. % of thickener and the present partially hydrogenated farnesene composition as a minor component. In certain embodiments, one or more thickeners are included in the composition/product as a minor component. For example, a composition/product can comprise less than about 50, 45, 40, 35, 30, 25, 20, 15, 10, 5, 4, 3, 2, or 1 wt. % of thickener and any suitable amount of the present partially hydrogenated farnesene composition. In certain embodiments, a composition/product comprises one or more thickeners in any suitable range selected anywhere between about 0.1 wt. % to less than about 50 wt. %, typically between about 1 wt. % to less than about 50 wt. %, based on the total weight of the composition. The amount of thickener (s) added to the composition/product depends on end use or application of the composition/product. For example, about 90 wt. % of the partially hydrogenated farnesene and about 10 wt. % thickener can be mixed together to make a metal cleaner as shown in Example 24.

In certain embodiments, a composition/product may further comprise one or more components and/or additives described herein at suitable proportions to provide desired properties to the composition/product.

While the amount or amount ranges of partially hydrogenated compositions and components/additives are described herein using the term "about," the amount or amount ranges can include the exact amount or exact ranges recited herein.

The compositions/products of the present invention can be manufactured through typical processes such as mixing or blending the composition. Some or all of the ingredients can be mixed together at once, or in some embodiments, the compositions can be prepared through the sequential addition of ingredients to the mixing vessel with low or moderate shearing mixing with order of addition and temperature suitable for the selected ingredients.

In certain embodiments, the end product is in the form of a wipe which is impregnated with the present compositions. The wipe may be in any suitable form, such as nonwoven material, cloth, sponge, or any absorbent material which can be pre-moistened with the present compositions. In some embodiments, the end product may be stored in a container with an applicator, such as a spray nozzle.

In certain embodiments, a kit is provided herein with the present compositions. The kit may comprise the present compositions described herein and instructions for using the composition and/or product. For example, the kit embodiment may include instructions for using the composition neat or instructions for diluting the composition with water (or other suitable diluent) and the appropriate dilution ratio. The kit may further comprise a wipe that is dry or pre-moistened with the present compositions, gloves, or other accessory items.

As for the performance of the solvent compositions provided herein as formulation ingredients, they are fully compatible with a wide range of consumer products, including, but not limited to hard surface heavy duty cleaners, hand cleaners, graffiti removers, crayon/pen ink removers, bug and tar removers, engine degreasers, laundry pre-spotters, oven cleaners, auto interior cleaners, all-purpose cleaner concentrates and metal cleaning fluids, adhesive removers and paint strippers. The solvent compositions are also fully compatible with a wide range of personal care products, such as night cream, anti-frizz, lip gloss, and nail polish removers.

The materials described herein are also expected to provide a significant benefit to the applications for pesticides and insecticides, hot melt adhesives, sealants, co-monomer in resins and elastomer formulations, synthetic base fluids for drilling mud applications, enhanced oil recovery, an additive in paints and coatings, wood treatment, a processing oil for plasticizing applications, a reactive diluent, a co-monomer in friedel crafts and radical polymerizations, lubricant and lubricant additive, a metathesis cross partner/substrate, a viscosity modifier, photo and temperature curable initiator system, a solvent and co-solvent for fragrance formulations, antibacterial and/or antifungal additive, and plasticizer in nail polish enamel.

EXAMPLES

As used herein, the symbols and conventions used in these processes, schemes and examples, regardless of whether a particular abbreviation is specifically defined, are intended to be consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); ppm (parts per million); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Examples 1-9

Partially Hydrogenated Farnesene Solvent Compositions

Compositions were prepared according to the description above. The compositions were evaluated by gas chromatography-FID. The compositions had the following components (wt. %):

| Example | Avg. MW | Avg. Dbl. Bonds | Farnesane | Hexahydro-farnesene | Tetrahydro-farnesene | Dihydro-farnesene | Bisabolene/Farnesene |
|---|---|---|---|---|---|---|---|
| 1 | 206.31 | 1.15 | 0 | 0.51 | 14.50 | 84.75 | 0.24 |
| 2 | 206.33 | 1.16 | 0 | 0.25 | 15.84 | 83.80 | ND |
| 3 | 206.41 | 1.20 | 0 | 0.79 | 19.03 | 79.94 | 0.24 |
| 4 | 206.42 | 1.21 | 0 | 0.92 | 19.41 | 79.45 | 0.23 |
| 5 | 206.43 | 1.21 | 0 | 0.97 | 19.60 | 79.21 | 0.22 |
| 6 | 206.44 | 1.22 | 0 | 1.24 | 19.85 | 78.70 | 0.21 |
| 7 | 206.44 | 1.22 | 0 | 1.59 | 18.99 | 79.22 | 0.20 |
| 8 | 206.47 | 1.23 | 0 | 1.91 | 19.79 | 78.12 | 0.18 |
| 9 | 206.07 | 1.04 | 0 | 0.43 | 3.18 | 96.06 | 0.33 |

In addition to Examples 1 through 9, a number of additional compositions were prepared and evaluated by gas chromatography-FID. The overall range of compositions that have been made are as follows:

|  | Farnesane | Hexahydro-farnesene | Tetrahydro-farnesene | Dihydro-farnesene | Farnesene |
|---|---|---|---|---|---|
| Min Value | 0.00 wt. % | 0.00 wt. % | 2.77 wt. % | 62.84 wt. % | 0.00 wt. % |
| Max Value | 0.28 wt. % | 3.05 wt. % | 33.96 wt. % | 96.33 wt. % | 0.36 wt. % |

Examples 1 through 9 and other similarly produced compositions were tested for their applicability as solvents and for other end uses. The compositions shown as Example 2 and Example 9 were selected as exemplary compositions to be formulated with other components/additives so that their performance can be tested by an independent third party laboratory. Exemplary compositions/products and their performance results tested by an independent third party laboratory are described below.

Example 10

Asphalt Removal Testing

The solvent composition of Example 2 was tested for cleaning efficiency of asphalt removal. Cleaning efficiency was evaluated in comparison to several known cleaning solvents.

The solvents were tested with a Gardner Blue Straight-Line Washability Machine. Armor Coat asphalt sealer (Lot#2505600120, LC#14-T0076) was applied to 15.0 cm×10.0 cm 304 SS brushed stainless steel panels using a Gardco Adjustable Film applicator. The applicator was set to a gap of 0.300 mm. The panels were placed into a forced air oven preheated to 1000° C. for two hours. The panels were removed and cooled under ambient conditions for a minimum of one hour prior to testing.

A small 3M cellulose sponge was conditioned according to ASTM D4488 A5. A soiled and aged panel was placed on the Gardner Straight-line washability apparatus using a template. 20 mL of a test solvent was applied to the preconditioned sponge. The sponge was inverted onto the asphalt soil. The Gardner machine was started and run until approximately 70-90% of the soil was removed by the test solvent. After the machine was stopped, the panel was rinsed with a cool stream of tap water. The panel was air dried.

Using a camera and lighting booth, a digital picture was taken of the cleaned panel. The imaged was analyzed with image analysis software to quantify the percentage of bitumen removed from the surface. The average percentage removed and the average number of cycles required to achieve the percentage removed are provided below:

| Solvent(s) | Avg. # of Cycles | Avg. % Removed | % Removed Std. Dev. |
|---|---|---|---|
| d-limonene | 88 | 78.0 | 5.64 |
| Example 2 | 169 | 74.3 | 4.68 |
| Example 2 + 30% d-limonene | 127 | 79.1 | 4.31 |
| Example 2 + 10% d-limonene | 153 | 76.1 | 2.19 |
| Aromatic 200 | 179 | 77.7 | 3.32 |
| Soya methyl ester | 340 | 68.8 | 5.48 |
| Isopar M | 333 | 73.6 | 10.05 |
| Example 2 + DBE-LVP (75:25 wt.) | 103 | 77.0 | 4.14 |
| Example 2 + ethyl lactate (75:25 wt.) | 200 | 79.9 | 0.99 |

As shown in the results above, the solvent composition of Example 2 and its blend showed cleaning efficiency comparable to, or better than, the standard cleaning solvents. The images of representative panels from asphalt cleaning study are shown in FIG. 1.

Example 11

White Lithium Grease Removal Testing

The composition of Example 2 shown above was tested for cleaning efficiency of white lithium grease removal. Cleaning efficiency was evaluated in comparison to several known cleaning solvents.

The solvents were tested with a Gardner Blue Straight-Line Washability Machine. General multi-purpose lithium grease (NLGI #3 grade lithium grease) was applied to 15.0 cm×10.0 cm 304 SS brushed stainless steel panels using a Gardco Adjustable Film applicator. The applicator was set to a gap of 0.400 mm. The panels were placed into a forced air oven preheated to 160° C. for eighteen hours. The panels were removed from the oven, and the oven was then heated to 190° C. The panels were returned to the oven for seven hours. The panels were removed and cooled under ambient conditions for a minimum of 90 minutes prior to testing.

A small 3M cellulose sponge was conditioned according to ASTM D4488 A5. A soiled and aged panel was placed on the Gardner Straight-line washability apparatus using a template. 20 mL of a test solvent was applied to the preconditioned sponge. The sponge was inverted onto the asphalt soil. The Gardner machine was started and run until approximately 70-90% of the soil was removed by the test solvent. After the machine was stopped, the panel was rinsed with a cool stream of tap water. The panel was air dried.

Using a camera and lighting booth, a digital picture was taken of the cleaned panel. The image was analyzed with image analysis software to quantify the percentage of bitumen removed from the surface. The results below provide the average percentage removed and the average number of cycles required to achieve the percentage removed.

| Solvent(s) | Avg. # of Cycles | Avg. % Removed | % Removed Std. Dev. |
|---|---|---|---|
| d-limonene | 7 | 85.4 | 7.82 |
| Isopar M | 15 | 96.5 | 1.72 |
| Example 2 | 7 | 82.5 | 3.41 |
| DBE-LVP | 238 | 57.3 | 40.86 |
| Aromatic 200 | 8 | 83.73 | 5.46 |
| Soya methyl ester | 23 | 84.23 | 2.33 |
| Ethyl lactate | 47 | 64.70 | 5.57 |
| Example 2 + 30% d-limonene | 6 | 82.37 | 2.35 |
| Example 2 + 10% d-limonene | 9 | 85.47 | 1.08 |
| Example 2 + ethyl lactate (75:25 wt.) | 7 | 81.0 | 9.01 |
| Example 2 + DBE-LVP (75:25 wt.) | 8 | 84.70 | 9.01 |

Figure 2:
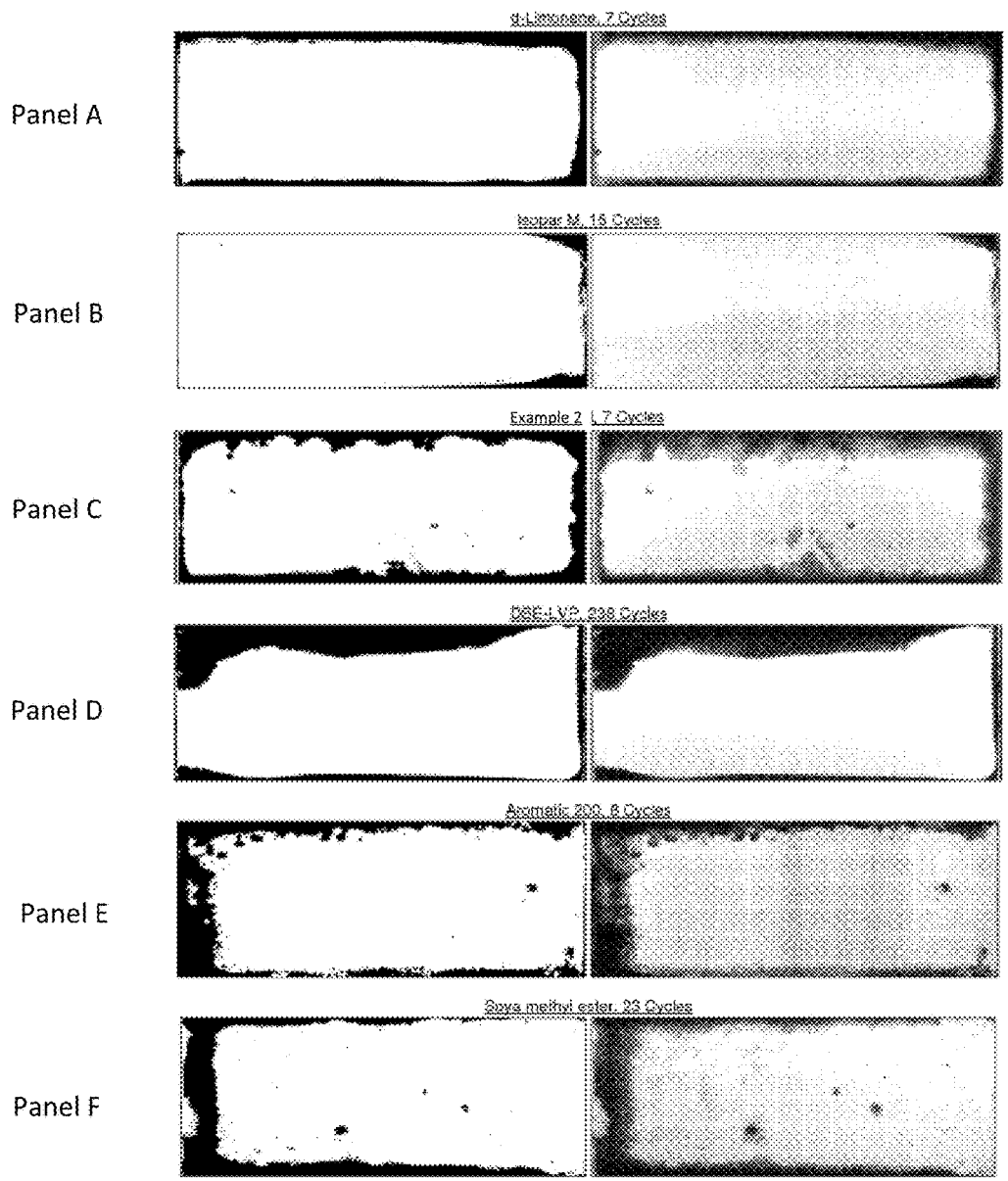
FIG. 2, panels A through K, provide lithium grease washing camera images (right panels) and images after processing with image analysis software (left panels).
Figure 2:
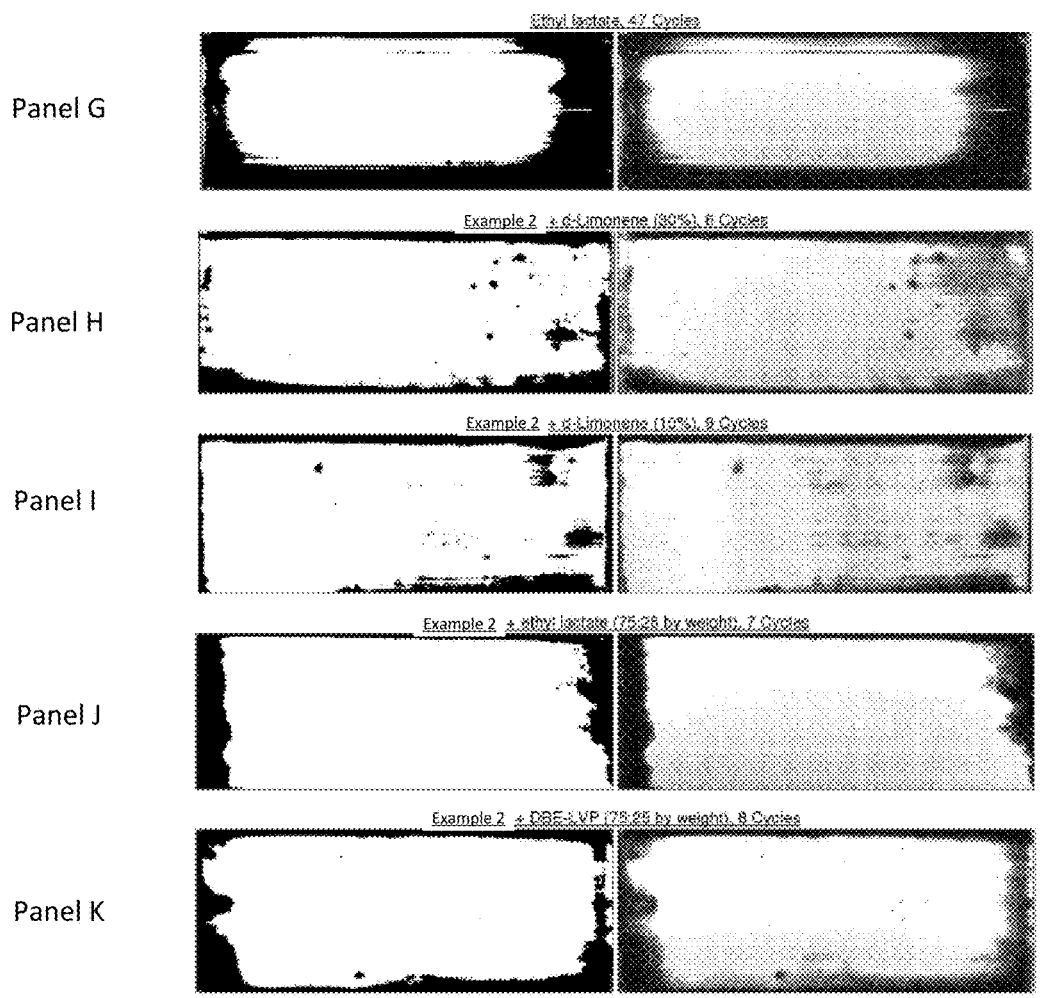

As shown in the results, the composition of Example 2 showed cleaning efficiency comparable to, or better than, the standard cleaning solvents. The images of representative panels from lithium grease cleaning study are shown in FIG. 2.

Example 12

Oxidative Stability

The oxidative stability of a composition provided herein was evaluated.

For each sample, a test composition was stored for 104 weeks at 25° C. The amount of composition remaining was tested and compared to the amount at the initial time. Further samples were stored for 6 days at 60° C. The amount of composition remaining was tested and compared to the amount at the initial time.

| Sample | 104 Weeks @ 25° C. | 6 Days @ 60° C. |
|---|---|---|
| Example 2 | 99.8% | 97.2% |
| d-Limonene | 24.0% | 52.3% |

Example 13 pH Stability

The pH stability of a composition provided herein was evaluated.

For each sample, a test composition was stored at the listed pH for 30 minutes at 25° C. The amount of composition remaining was tested and compared to the amount at the initial time.

| Sample | pH 1 | pH 4 | pH 13 |
|---|---|---|---|
| Example 2 | 99.88% | 99.9% | 99.98% |

Example 14

Hard Surface Heavy-Duty Cleaner

Provided here are two exemplary cleaning compositions for the cleaning of hard surfaces or substrates:

| Ingredient | Amount wt. % | Function |
|---|---|---|
| Example 2 | 50.0% | Solvent |
| Sodium lauryl ether sulfate (~60%) | 24.0% | Surfactant |
| Tomadol 25-3 | 10.0% | Surfactant |
| Tomadol 25-7 | 6.0% | Surfactant |
| Fatty Acid DEA | 10.0% | Surfactant |

| Hard Surface Heavy Duty Cleaner | | |
|---|---|---|
| Ingredient | Amount wt. % | Application |
| Example 2 | 35.0 | Solvent — For clean-up of heavy |
| Tomadol 25-7 | 3.0 | Surfactant — grease surfaces in |
| Videt ME-80 | 20 | Surfactant — industrial applications |
| Water | 42 | Diluent |

These cleaners can be used for cleaning heavy grease surfaces in industrial applications.

Example 15

Hand Cleaner

Provided here are two exemplary cleaning compositions for heavy-duty cleaning of hand surfaces:

| Composition 15A | | |
|---|---|---|
| Ingredient | Amount wt. % | Function |
| Example 2 | 25.0 | Solvent |
| Acrylates $C_{10-30}$ Cross polymer | 0.20 | Thickener |
| Deionized Water | 60.10 | Diluent |
| Propylene Glycol | 1.00 | Solvent |
| Glycerin | 1.00 | Moisturizer |
| Methyl Gluceth-20 | 1.00 | Wetting Agent |
| Germaben | 1.00 | Preservative |
| NaOH (20%) | ~0.70 (to pH 5.5-6.0) | pH Adjustment |
| Pumice | 10.00 | Exfoliant |

| Composition 15B | | |
|---|---|---|
| Ingredient | Amount wt. % | Application |
| Example 2 | 6.0 | Solvent — A waterless hand |
| Acrylates $C_{10-30}$ Cross polymer | 0.20 | Thickener — cleaner containing |
| Water | 83.65 | Diluent — abrasive for heavy |
| Alcogum SL-70 | 1.25 | Surfactant — duty cleaning in |
| Glycerin | 1.0 | Humectant — industrial environments |
| Tomadol 25-7 | 1.75 | Surfactant |

-continued

| Composition 15B | | |
|---|---|---|
| Ingredient | Amount wt. % | Application |
| Triethanolamine (to pH 7.0-7.9) | 0.5 | Neutralizer |
| Pumice | 4.5 | Abrasive |
| Microcare MTO | 0.15 | Preservative |
| d-Limonene | ≤1.9 | Fragrance |

These compositions can be used as a waterless hand cleaner and sanitizer with or without an abrasive, and is useful for heavy duty cleaning in industrial environments The second formula of the hand cleaner incorporating Example 2 (i.e., Composition 15B) was tested for cleaning efficiency utilizing ASTM D4488-95-A6. Cleaning efficiency was evaluated in comparison to a commercially available and leading brand hand cleaner.

The hand cleaner was tested with a Gardner Blue Straight-Line Washability Machine.

Panel preparation: Stainless steel sheeting was cut into 6"×6" squares. Panels were cleaned with a paper towel and acetone to remove any oil finish and dust from the panels. White semi-gloss paint was applied to cleaned panels. Panels were then air-dried for 7 hours and placed in a 54.5° C. oven for 16 hours. The panels were cooled at room temperature for 7 hours prior to use.

Soil Application: The panels were separately stained with the soil mixture by applying the soil to a paint applicator, which was then drawn across the prepared panel as many times as needed to get a consistent application of soil. The final soiled area was 2.5" wide and ran the length of the panel. The panels were then placed into an oven at 54.5° C. for 16-17 hours.

Colorimeter Measurements: After proper calibration of the CR-410 Colorimeter, its data processor was set to Y mode. For this test, it was only necessary to use the "Y" value. Reflectance of the steel panels was read before and after soiling by taking 5 readings per panel perpendicularly across the grain of the test area. An average was calculated from the 5 readings and was used in the calculation of results.

Cleaning test: The products were tested as received (RTU). Soiled panels were placed on the scrubbing machine and fastened to the base with a C-clamp. 10 g of the test gel was evenly applied onto a clean, damp cellulose sponge and inverted so that the wet side was in contact with the soiled panel, then scrubbed for 9 cycles. The panel was removed, rinsed lightly with cool tap water and air dried. % Cleaning Efficiency (C.E.)=(Rc−Rs)/(Ro−Rs)×100 Where Rc=cleaned reflectance; Ro=original reflectance; and Rs=soiled reflectance.

| Sample | Avg. C.E. % |
|---|---|
| Hand Cleaner LC#142J2611 | 60.3 |
| Fast Orange Microgel Hand Cleaner (with pumice) LC#14-T0512 | 39.3 |

Figure 3:
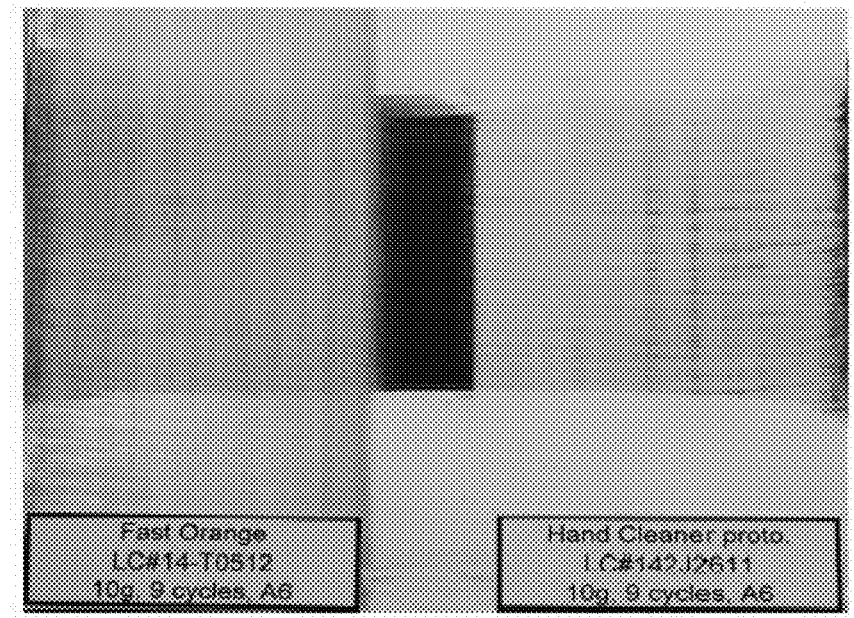
FIG. 3 illustrates a photograph showing a soiled panel cleaned with a hand cleaner formulation according to one embodiment provided herein and a similarly soiled panel cleaned with a commercially available hand cleaner.

The photographs of representative panels cleaned with the hand cleaners shown in the above table are illustrated in FIG. 3. As shown in FIG. 3, the composition according to the present embodiment (Hand Cleaner LC#142J2611) showed cleaning efficiency comparable to, or better than, the commercially available cleaner.

The second formula of the hand cleaner incorporating Example 2 (Composition 15B) was also tested for cleaning efficiency utilizing CSPA DCC-17. Cleaning efficiency was evaluated in comparison to a commercially available and leading brand hand cleaner.

Panel Preparation: Masonite tiles were cleaned with a light duty dilution of hand dish detergent and panels were air dried.

Ink/Marker Application: A double application of each marker was applied in a uniform straight line along the long edge of the Masonite tile, with each line spaced one inch apart. The soiled substrate was allowed to dry overnight at room temperature.

Cleaning test: A clean conditioned sponge was used for each cleaning procedure. 10 grams of cleaner was dispensed onto the damp sponge (sponge and holder weigh about 350 grams). The sponge was placed so that the manufactured edge was the scrubbing surface. The tile in the apparatus was placed so that scrubbing action was perpendicular to the direction of the soiling. The wash apparatus was operated over the soiled area for a total of 25 cycles. The test area was rinsed with cool tap water.

Evaluation: A group of 2 panelists evaluated the cleaned areas to determine the percentage of cleaning achieved for each marker. An average of each rating is reported.

| Sample | Dilution | Marker | Avg. Rating |
|---|---|---|---|
| Permatex Fast Orange Microgel Hand Cleaner LC#14-T0512 | RTU | Black | 53 |
| | | Red | 73 |
| | | Blue | 70 |
| | | Green | 78 |
| Hand Cleaner LC#142J2611 | RTU | Black | 67 |
| | | Red | 75 |
| | | Blue | 75 |
| | | Green | 82 |

Figure 4:
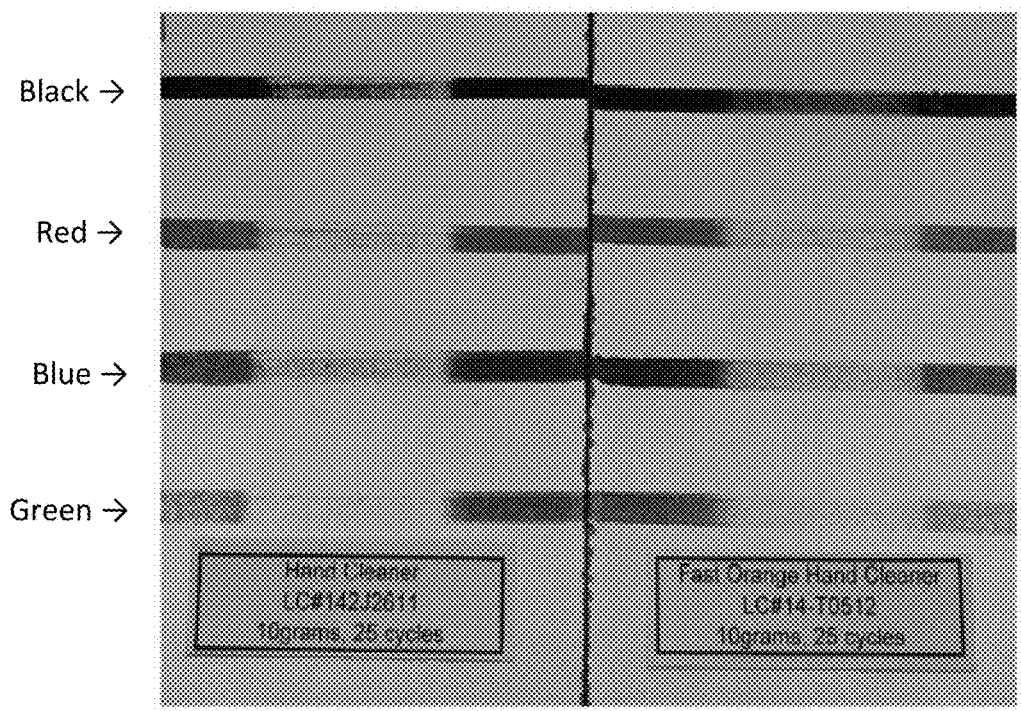
FIG. 4 illustrates a photograph of a panel with ink marker lines cleaned with a hand cleaner formulation according to one embodiment provided herein and a similarly soiled panel cleaned with a commercially available hand cleaner.

The cleaning test results shown in the above table are also illustrated in representative cleaned tiles shown in FIG. 4. FIG. 4 illustrates that the hand cleaner according the present embodiment (Hand Cleaner LC#142J2611) showed cleaning efficiency comparable to, or better than, the commercially available product.

Example 16

Graffiti Remover

Provided here are two exemplary cleaning compositions for heavy-duty cleaning of hard surfaces:

| Ingredient | Amount | Function |
|---|---|---|
| Example 2 | 65.0% | Solvent |
| Laureth-7 | 25.00% | Surfactant |
| Propylene Glycol | 10.00% | Carrier |

| Graffiti Remover | | | |
|---|---|---|---|
| Ingredient | Amount % | Function | Application |
| Example 2 | 18.0 | Solvent | A cleaner for removing graffiti from painted surfaces |
| Tomadol 25-7 | 0.9 | Surfactant | |
| DBE-LVP | 18.0 | Solvent | |
| Isopar M | 63.1 | Solvent/Diluent | |

These compositions provide cleaners for removing graffiti from painted substrates or surfaces.

Example 17

Solvent Degreaser and Ink Remover

Provided here are two exemplary cleaning compositions for cleaning or removing crayon or pen marks from surfaces or substrates:

| Composition 17A | | |
|---|---|---|
| Ingredients | Amount (wt. %) | Function |
| Example 2 | 69.0% | Solvent |
| Laureth-7 | 10.00% | Emulsifier |
| Cocamide DEA | 1.00% | Emulsifier |
| Propylene Glycol | 10.00% | Carrier |
| Water | 10.00% | Carrier |

| Composition 17B Solvent Degreaser (composition LC#142J2701) | | | |
|---|---|---|---|
| Ingredient | Amount wt. % | Function | Application |
| Example 2 | 9 | Solvent | A cleaner for removing crayon and pens from painted walls and interior surfaces |
| DBE-LVP | 9 | Solvent | |
| Rhodocal IPAM | 0.3 | Surfactant | |
| Isopar M | 81.7 | Solvent/Diluent | |
| d-Limonene | Optional 0-2% | Fragrance | |

These compositions provide spray-on cleaners for removing crayon and pen marks from painted surfaces or substrates, for instance, painted interior walls.

The second formula of the crayon and ink remover incorporating Example 2 (Composition 17B-LC#142J2701) was tested for cleaning efficiency of permanent markers utilizing modified CSPA DCC-17. Cleaning efficiency was evaluated in comparison to a commercially available crayon and ink remover.

Panel Preparation: Masonite tiles were cleaned with a light duty dilution of hand dish detergent and panels were air dried.

Ink/Marker Application: A double application of each marker was applied in a uniform straight line along the long edge of the Masonite tile, with each line spaced one inch apart. The soiled substrate was allowed to dry overnight at room temperature.

Cleaning test: A clean conditioned sponge was used for each cleaning procedure. 20 mL of cleaner was dispensed onto the damp sponge to absorb the test solution (sponge and holder weigh about 350 grams). The sponge was placed so that the manufactured edge is the scrubbing surface. The tile in the apparatus was placed so that scrubbing action is perpendicular to the direction of the soiling. The wash apparatus was operated over the soiled area and scrubbing was continued until approximately 80% removal was achieved. The test area was rinsed with cool tap water.

Evaluation: A group of 2 panelists evaluated the cleaned areas using the below rating system. An average of each rating is reported.
5=total soil removal without streaking
4=near total soil removal with streaking
3=good soil removal
2=moderate soil removal
1=poor soil removal
0=null soil removal

| Sample | Dilution | Avg. Rating |
|---|---|---|
| Goo Gone Cleaner LC#14-T0513 | RTU | 0 (approx. 0-5% removal) |
| Crayon/Ink Remover LC#142J2701 | RTU | 4 (approx. 90-95% removal) |

Figure 5:
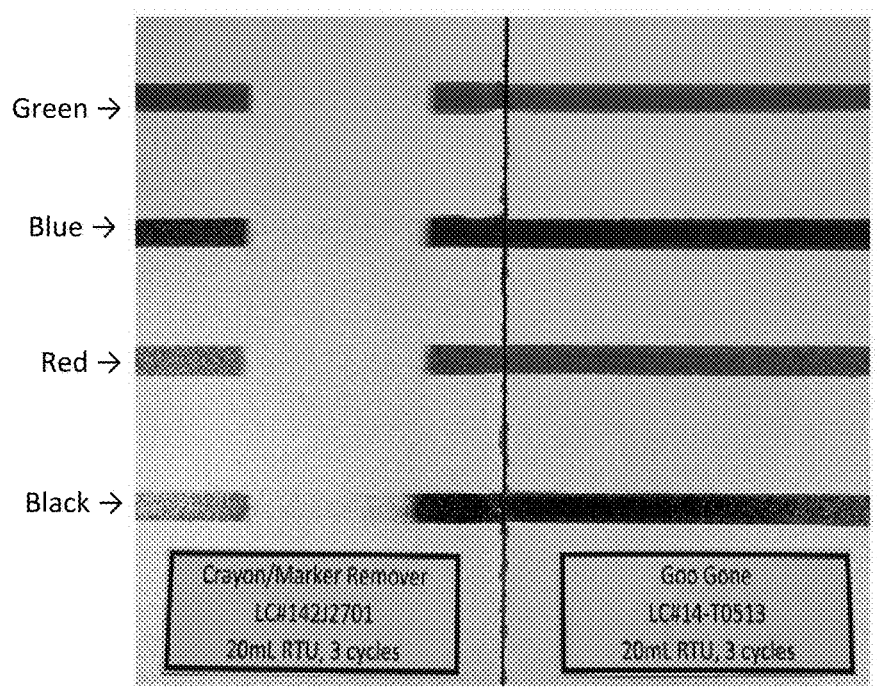
FIG. 5 illustrates a photograph of a panel soiled with ink marker lines cleaned with a degreaser remover formulation according to one embodiment provided herein and a similarly soiled panel cleaned with a commercially available ink remover product.

The photograph of representative tiles that were cleaned with the cleansers in the above table is shown in FIG. 5. As shown in FIG. 5, the composition according to the present invention (Crayon/Marker Remover LC#142J2701) showed cleaning efficiency better than the commercially available product.

The second formula of the crayon and ink remover incorporating Example 2 (i.e., composition 17B) was tested for cleaning efficiency of wax crayons utilizing CSPA DCC-17. Cleaning efficiency was evaluated in comparison to a commercially available and leading brand hand cleaner.

Panel Preparation: The Masonite tiles were cleaned with a light duty dilution of hand dish detergent and panels were air dried.

Crayon Application: A double application was applied of each waxy crayon in a uniform straight line along the long edge of the Masonite tile, with each line spaced one inch apart. The soiled substrate was allowed to dry overnight at room temperature.

Cleaning test: A clean conditioned sponge was used for each cleaning procedure. 20 mL of cleaner was dispensed onto the damp sponge to absorb the test solution (sponge and holder weigh about 350 grams). The sponge was placed so that the manufactured edge was the scrubbing surface. The tile was placed in the apparatus so that scrubbing action was perpendicular to the direction of the soiling. The wash apparatus was operated over the soiled area and scrubbing continued until approximately 80% removal was achieved. The test area was then rinsed with cool tap water.

Evaluation: A group of 2 panelists evaluated the cleaned areas using the below rating system. An average of each rating is reported.
5=total soil removal without streaking
4=near total soil removal with streaking
3=good soil removal
2=moderate soil removal
1=poor soil removal
0=null soil removal

| Sample | Dilution | Avg. Rating |
|---|---|---|
| Goo Gone Cleaner LC#14-T0513 | RTU | 4 (approx. 90% removal) |
| Crayon/Ink Remover LC#142J2701 | RTU | 3 (approx. 80% removal) |

Figure 6:
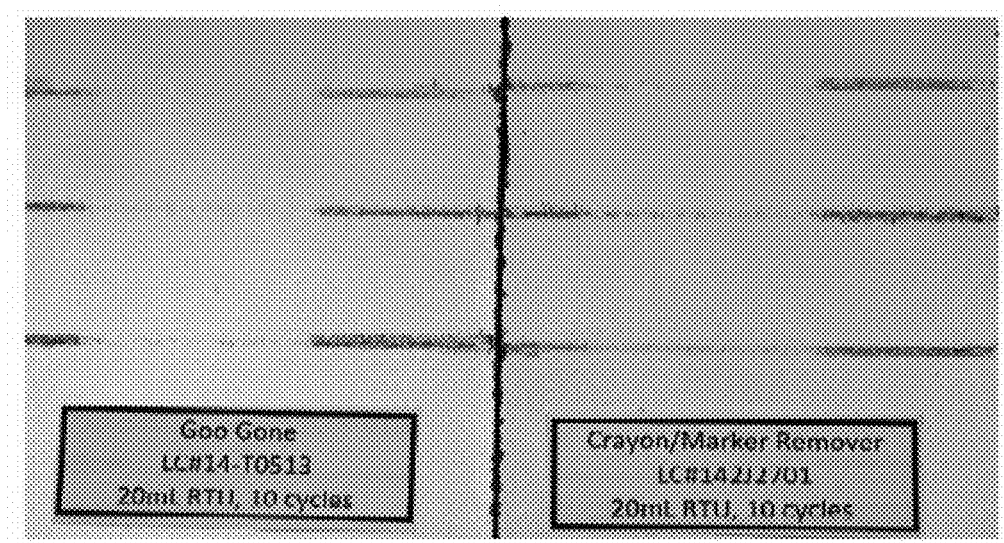
FIG. 6 illustrates a photograph of a panel soiled with crayon lines cleaned with a degreaser formulation according to one embodiment provided herein and a similarly soiled panel cleaned with a commercially available cleaning product.

The photograph of representative tiles cleaned with the cleaners shown in the above table is illustrated in FIG. 6. As shown in FIG. 6, the composition according to the present invention (Crayon/Ink Remover LC#142J2701) showed cleaning efficiency comparable to the commercially available product.

Example 18

Bug or Tar Remover (Exterior Auto Cleaner)

Provided here are two exemplary cleaning compositions for cleaning or removing bugs or tar from surfaces or substrates:

| Ingredient | Amount | Function |
|---|---|---|
| Example 2 | 15.00% | Solvent |
| Steposol ® DG | 8.00% | Emulsifier |
| Sodium Citrate | 1.00% | pH adjustment |
| Sodium Gluconate | 7.00% | Chelator |
| Water | 69.00% | Carrier |

Bug and Tar Remover

| Ingredient | Amount wt. % | Function | Application |
|---|---|---|---|
| Example 2 | 35 | Solvent | Heavy duty external car cleaner for removal of bugs and tar from automotive vehicles |
| Tomadol 25-7 | 3.0 | Surfactant | |
| Videt ME-80 | 20.0 | Surfactant | |
| Water | 42.0 | Diluent | |

These compositions provide heavy duty external cleaners for removal of bugs and tar from substrates or surfaces of vehicles such as trucks.

Example 19

All Purpose Cleaner and Engine Degreaser

Provided here are seven exemplary cleaning compositions for degreasing surfaces or substrates of engines or engine components:

Engine Degreaser #A

| Ingredient | Amount | Function |
|---|---|---|
| Water | 82.0% | Solvent |
| Sodium metasilicate pentahydrate | 2.00% | Oil Cutter |
| Potassium hydroxide (45%) | 2.00% | pH adjustment |
| Example 2 | 8.00% | Solvent |
| Tomadyne 100 surfactant | 6.00% | Emulsifier |

Engine Degreaser #B

| Ingredient | Amount wt. % | Function | Application |
|---|---|---|---|
| Water | 90.25 | Diluent | A degreaser for basic engine cleaning |
| Sodium Metasilicate Pentahydrate | 2.0 | Alkaline Buffer | |
| Potassium Hydroxide (45%) | 2.0 | Alkaline Builder | |
| Example 2 | 0.75 | Solvent | |
| Videt Q3 | 4.0 | Surfactant | |
| Trilon M liquid | 1.0 | Chelator | |

Aqueous Engine Degreaser #1

| Ingredient | Amount wt. % | | Application |
|---|---|---|---|
| Water | 90.2 | Diluent | Formulation for Heavy duty industrial cleaning applications pH ~13-14, Cloud point = 51° C. |
| Sodium Metasilicate Pentahydrate | 2.0 | Alkaline Buffer | |
| Potassium Hydroxide (45%) | 2.0 | Alkaline Builder | |
| Example 2 | 0.75 | Solvent | |
| Videt Q3 | 4.1 | Surfactant | |
| Trilon M liquid | 1.0 | Chelator | |

Aqueous Engine Degreaser #2

| Ingredient | Amount wt. % | | Application |
|---|---|---|---|
| Water | 91.9 | Diluent | Formulation for Heavy duty industrial cleaning applications pH ~11, Cloud point = 35° C. |
| Trilon M liquid | 0.5 | Chelator | |
| Potassuim Carbonate | 0.6 | Alkaline Builder | |
| Tergitol 15-S-7 | 4.0 | Surfactant | |
| Amphoteric 400 | 2 | Surfactant | |
| Example 2 | 1 | Solvent | |

Aqueous Engine Degreaser #3

| Ingredient | Amount wt. % | | Application |
|---|---|---|---|
| Water | 92.9 | Diluent | Formulation for Heavy duty industrial cleaning applications pH ~11, Cloud point = 40° C. |
| Trilon M liquid | 0.5 | Chelator | |
| Potassuim Carbonate | 0.6 | Alkaline Builder | |
| Ecosurf EH-6 | 4.0 | Surfactant | |
| Amphoteric 400 | 1 | Surfactant | |
| Example 2 | 1 | Solvent | |

Aqueous Engine Degreaser #4

| Ingredient | Amount wt. % | | Application |
|---|---|---|---|
| Water | 91.9 | Diluent | Formulation for Heavy duty industrial cleaning applications pH ~11, Cloud point = 34° C. |
| Trilon M liquid | 0.5 | Chelator | |
| Potassuim Carbonate | 0.6 | Alkaline Builder | |
| Ecosurf SA-7 | 4.0 | Surfactant | |
| Amphoteric 400 | 2 | Surfactant | |
| Example 2 | 1 | Solvent | |

Aqueous Engine Degreaser #5

| Ingredient | Amount wt. % | | Application |
|---|---|---|---|
| Water | 90.9 | Diluent | Formulation for Heavy duty industrial cleaning applications pH ~11, Cloud point = 45° C. |
| Trilon M liquid | 0.5 | Chelator | |
| Potassuim Carbonate | 0.6 | Alkaline Builder | |
| Tergitol 15-S-7 | 4.0 | Surfactant | |
| Alkatrope SXS-40 | 3.0 | Surfactant | |
| Example 2 | 1.0 | Solvent | |

To make the composition labeled Engine Degreaser #A shown above, sodium metasilicate pentahydrate was added to water and mixed until dissolved. Potassium hydroxide was then added and mixed. The composition of Example 2 was added and mixed. Then, Tomadyne 100 was added and mixed. This composition provides an all-purpose cleaner and degreaser for basic engine cleaning The second formula of the all-purpose cleaner and engine degreaser incorporating Example 2 (i.e., Engine Degreaser #B) was tested for cleaning efficiency of crude oil/bitumen utilizing ASTM D4488 A5. Cleaning efficiency was evaluated in comparison to a commercially available and leading brand cleaner.

Crude oil application: A small amount of crude oil was applied with a small pipette to the center of the automotive painted steel panel. Using a lens wipe, the oil was leveled into a uniform coating. The soiled panel was placed onto an aluminum tray and transferred to a preheated oven set to 400° C. After 48 hours, the panels were removed and cooled to ambient conditions for a minimum of ninety minutes prior to testing.

Cleaning Test: A small cellulose sponge was conditioned as per ASTM D4488 A5 Method. The soiled and aged panel was placed on the Gardner Straight-line washability apparatus using a template. 10.0 milliliters of the test product was applied to the preconditioned sponge and the sponge was inverted onto the soil. The Gardner machine was started and ran until approximately 70-90% of the soil had been removed by the test product. After the machine was stopped, the panel was rinsed with a cool stream of tap water and air dried.

Evaluation: Using the Nikon camera and lighting booth, a digital picture of the cleaned panel was taken. The image was analyzed using the image analysis software to quantify the percentage of bitumen removed from the surface. The average percentage removed and the number of cycles required to achieve the percentage removed is reported below.

| Products | # of cycles | Avg. % Removal | % Removal Std. Dev. |
|---|---|---|---|
| Super Clean Tough Task Cleaner-Degreaser LC#13-T1040 | 30 | 66.4 | 1.8 |
| Prototype Cleaner-Degreaser LC#142J2302 | 30 | 83.9 | 11.7 |

Figure 7:
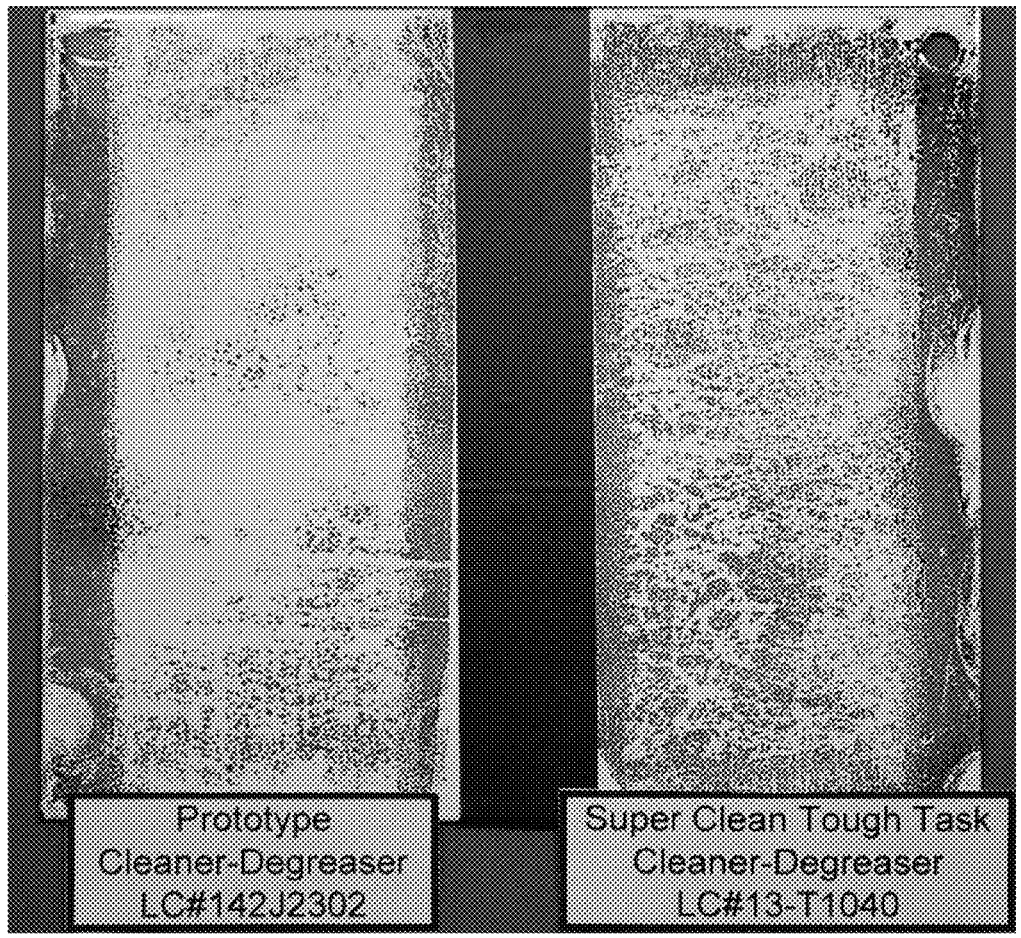
FIG. 7 illustrates a photograph of soiled steel panel cleaned with a degreaser formulation according to one embodiment provided herein and a similarly soiled panel cleaned with a commercially available degreaser product.

The photograph of representative panels cleaned with the cleaning products shown in the above table is illustrated in FIG. 7. As shown in FIG. 7, the composition according to the present invention (LC#142J2302) showed cleaning efficiency comparable to, or better than, the commercially available product.

The second formula of the all-purpose cleaner and engine degreaser incorporating Example 2 (i.e., Example Degreaser #B) was tested for cleaning efficiency of soil mixture utilizing ASTM D4488 A5. Cleaning efficiency was evaluated in comparison to a commercially available and leading brand cleaner.

Panel Preparation: Stainless steel sheeting was cut into 6"×6" squares. Panels were cleaned with a paper towel and acetone to remove any oil finish and dust from the panels. White semi-gloss paint was applied to cleaned panels and air-dried for 7 hours and placed in a 54.5° C. oven for 16 hours. Panels were cooled at room temperature for 7 hours prior to use.

Soil Application: The panels were separately stained with the soil mixture by applying the soil to a paint applicator, which was then drawn across the prepared panel as many times as needed to get a consistent application of soil. The final soiled area was 2.5" wide and ran the length of the panel. The panels were then placed onto an oven at 54.5° C. for 16-17 hours.

Colorimeter Measurements: After proper calibration of the CR-410 Colorimeter, the data processor was set to Y mode. For this test it was only necessary to use the "Y" value. The reflectance of steel panels was read before and after soiling by taking 5 readings per panel perpendicularly across the grain of the test area. An average was calculated from the 5 readings and was used in the calculation of results.

Cleaning test: The products were tested as received (RTU). A soiled panel was placed on the scrubbing machine and fastened to the base with a C-clamp. 10 ml of the test solution was applied onto a clean, damp cellulose sponge and inverted so that the wet side was in contact with the soiled panel, and scrubbed for 2 cycles. The panel was removed and rinsed lightly with cool tap water and air dried.

Cleaning Efficiency (C.E.)=(Rc−Rs)/(Ro−Rs)×100 where Rc=cleaned reflectance; Ro=original reflectance; and Rs=soiled reflectance.

| Sample | Avg. C.E. % |
|---|---|
| Engine Degreaser LC#142J2302 | 65.2 |
| Super Clean Tough Task Cleaner-Degreaser LC#13-T0140 | 63.9 |

Figure 8:
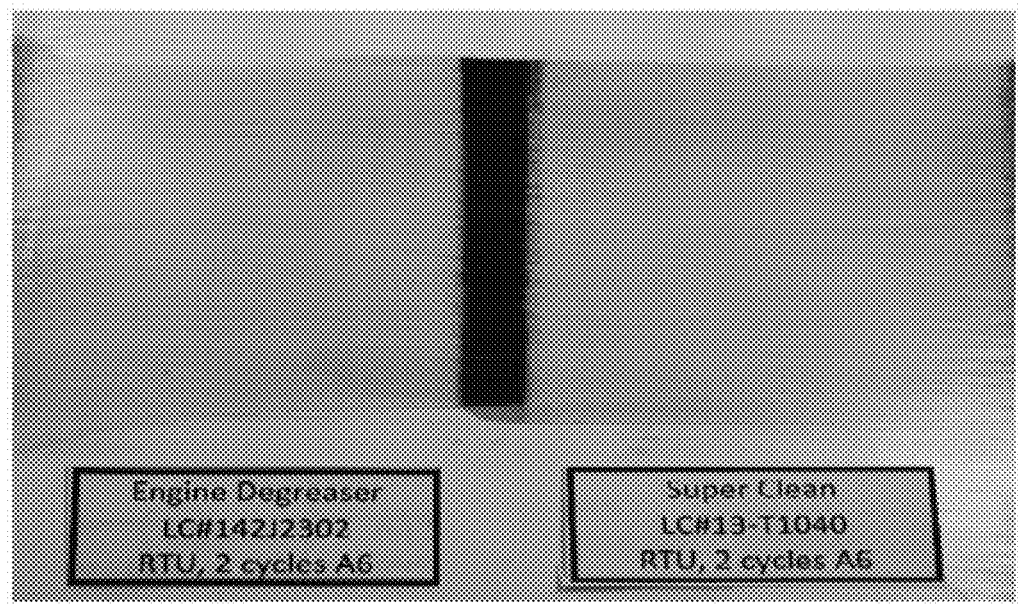
FIG. 8 illustrates a photograph of a soiled panel cleaned with an engine degreaser formulation according to one embodiment provided herein and a similarly soiled panel cleaned with a commercially available degreaser product.

The photograph of representative panels that were cleaned with degreaser products shown in the above table is shown in FIG. 8. As shown in FIG. 8, the composition according to the present invention (Engine Degreaser LC#142J2302) showed degreasing efficiency comparable to, or better than, the commercially available product.

Example 20

Laundry Pre-Spotter

Provided here is an exemplary cleaning composition for cleaning or pre-cleaning laundry stains from cloth surfaces or substrates, such as clothing surfaces and substrates:

| Ingredient | Amount | Function |
|---|---|---|
| Example 2 | 50% | Solvent |
| Linear Alcohol ($C_{12-15}$) Ethoxylate, POE-7 | 20% | Emulsifier |
| Linear Alcohol ($C_{12-15}$) Ethoxylate, POE-3 | 20% | Emulsifier |
| Ethanol | 4% | Solvent |
| Water | 6% | Carrier |

This composition can be applied to stains on laundry prior to washing to facilitate stain removal and/or cleaning.

Example 21

Oven Cleaner

Provided here is an exemplary cleaning composition for cleaning surfaces or substrates of ovens:

| Composition 21A | | |
|---|---|---|
| Ingredient | Amount | Function |
| Water | 73% | Carrier |
| Example 2 | 9.9% | Solvent |
| Cocamide DEA | 9.8% | Emulsifier |
| Sodium Branched Dodecyl Benzene Sulfonate | 2.4% | Emulsifier |
| d-limonene | 4.9% | Solvent |

| Composition 21B Oven Cleaner | | | |
|---|---|---|---|
| Ingredient | Amounts wt % | Function | Application |
| Water | 86 | Diluent | Spray cleaner to |
| Example 2 | 2.0 | Solvent | help remove stains |

-continued

Composition 21B
Oven Cleaner

| Ingredient | Amounts wt % | Function | Application |
|---|---|---|---|
| Kelzan ASX-T | 0.35 | Thickener | on household ovens |
| Sodium Bicarbonate | 2.0 | Alkaline Buffer | |
| Sodium Metasilicate Pentahydrate | 0.2 | Alkaline Buffer | |
| Trilon M liquid | 0.25 | Chelator | |
| Videt Q3 | 5.0 | Surfactant | |
| Potassium Hydroxide (45%) | 2.5 | Alkaline Builder | |

These compositions provide spray-on cleaners that can be used to clean surfaces or substrates of household ovens.

The second formula of the oven cleaner incorporating Example 2 (i.e., Composition 21B) was tested for cleaning efficiency of A-A-7B Alkaline Cleaner-Degreaser of Ovens, Grills, and Washable Surfaces. Cleaning efficiency was evaluated in comparison to a commercially available and leading brand cleaner.

Procedure: A mixture of butter, sugar, flour, and water was spread on porcelain enamel tiles at a rate of 0.80 grams per 20 square inches. The tiles were baked at 375° F. for 120 minutes and cooled to room temperature before use. Two tiles were placed in a vertical position and sprayed with the cleaner until a uniform coverage was obtained, and then the tiled were allowed to sit for 30 minutes. After 30 minutes, the 2 tiles were lightly rubbed with a damp sponge and then flushed with water. The panels were dried and the cleaning was repeated.

| Sample | Pass | % Removal (approx.) |
|---|---|---|
| Easy-Off Heavy Duty Oven Cleaner LC#14-T0540 | ≥75% | 100 |
| Prototype Oven Cleaner LC#142J2303 | | 100 |

Figure 9:
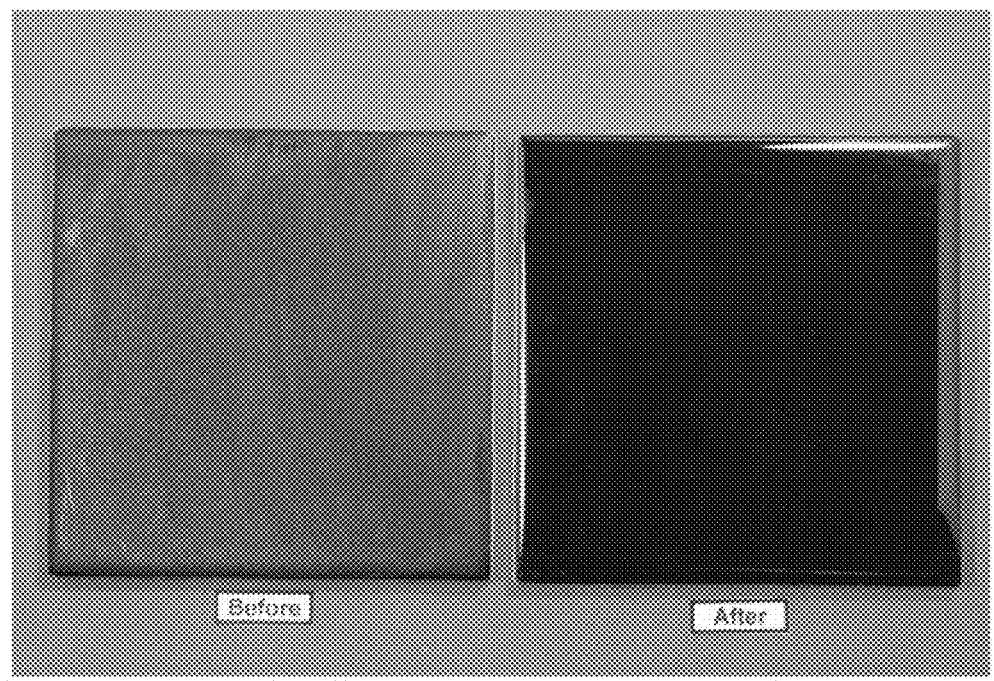
FIG. 9 illustrates a photograph of a soiled porcelain enamel tile before and after cleaning with a spray-on cleaner according to one embodiment provided herein.

The photograph shown in FIG. 9 illustrates a representative soiled tile before and after cleaning with the composition in accordance with the present invention (LC#142J2303).

Example 22

Interior Auto Cleaner

Provided here is an exemplary cleaning composition for cleaning interior surfaces or substrates of automobiles:

| Ingredient | Amount | Function |
|---|---|---|
| Deionized water | to 100% | Carrier/solvent |
| Sodium citrate | 1.00% | Detergent builder |
| Example 2 | 0.50% | Solvent |
| AMPHOSOL ® CA | 3.00% | Primary cleaning agent |
| Preservative | as needed | |

This composition provides a spray-on cleaner for cleaning interior surfaces or substrates of automobiles.

Example 23

All-Purpose Cleaner Concentrate

Provided here are exemplary concentrated cleaning compositions:

| Ingredient | Amount | Function |
|---|---|---|
| Example 2 | 9.00% | Solvent |
| Limonene | 1.50% | Solvent |
| Cocamide DEA | 65.00% | Surfactant |
| Coconut Fatty Acids | 6.00% | Solvent |
| TEA | 3.00% | pH Adjuster |
| Propylene Glycol | 6.00% | Carrier |
| Water | 9.50% | Carrier |

All-Purpose Cleaner Concentrate

| Ingredient | Amount % | Function | Application |
|---|---|---|---|
| Example 2 | 9.0 | Solvent | Dilutable formulation for light duty industrial cleaning applications |
| Videt ME-80 | 20 | Surfactant | |
| Tomadol 25-7 | 3.0 | Surfactant | |
| Water | 9.5 | Diluent | |

These compositions can be diluted for cleaning of, for example, light industrial substrates, floors, and surfaces.

Example 24

Metal Cleaner

Provided here is an exemplary cleaning composition for cleaning metal surfaces or substrates:

| Ingredient | Amount | Function |
|---|---|---|
| Example 2 | 90.00% | Solvent |
| Linear Alcohol Ethoxylate $C_{12}$-$C_{14}$, POE 7 | 10.00% | Thickener |

This composition provides a cleaner useful, for example, for substrates or surfaces of post-machining metal parts.

Example 25

Personal Care Products: Night Cream, Anti-Frizz, and Lip Gloss

Provided here are exemplary personal care products:
Night Cream:

| Item No. | Trade Name/Supplier | INCI Name | % by weight |
|---|---|---|---|
| | Phase A | | |
| 1 | Abil WE-09 (Evonik) | Polyglyceryl-4 Isostearate, Cetyl PEG/PPG-10/1 Dimethicone, Hexyl Laurate | 5.00% |
| 2 | Example 2 | Hydrogenated Farnesene | 15.00% |
| 3 | Abil Wax 9801 (Evnoik) | Cetyl Dimethicone | 2.00% |
| | Phase B | | |
| 4 | Deionized water | Water (Aqua) | 73.00% |
| 5 | Sodium Chloride (Univar) | Sodium Chloride | 1.00% |
| 6 | 1,3,Butylene Glycol (Univar) | Butylene Glycol | 3.00% |
| 7 | Mikrokill COS (Arch) | Phenoxyethanol, Chlorphenesin, Caprylyl Glycol | 1.00% |
| | Total | | 100.00% |

Anti-Frizz Treatment:

| Item No. | Trade Name/Supplier | INCI Name | % by weight |
|---|---|---|---|
| 1 | Example 2 | Hydrogenated Farnesene | 40.00% |
| 2 | Dow Corning 1403 (Dow Corning) | Dimethicone, Dimethiconol | 50.00% |
| 3 | Dow Corning 556 (Cow Corning) | Phenyl Trimethicone | 5.00% |
| 4 | Crodamol STS (Croda) | PPG-3 Benzyl Ether Myristate | 5.00% |
|   |   | Total | 100.00% |

Lip Gloss:

| Item No. | Trade Name/Supplier | INCI Name | % by weight |
|---|---|---|---|
| | Phase A | | |
| 1 | Example 2 | Hydrogenated Farnesene | 18.00% |
| 2 | Versagel ME-750 (Calumet/Penreco) | Hydrogenated Polyisobutene, Butylene/Ethylene/Styrene Copolymer, Ethylene/Propylene/Styrene Copolymer | 24.90% |
| 3 | Softisan 649 (Sasol) | Bis-Diglyceryl Polyacyladipate-2 | 16.00% |
| 4 | Crodamol PTIS (Croda) | Pentaerythrityl Tetraisostearate | 12.00% |
| 5 | Indopol H-100 (Lipo) | Polybutene | 15.00% |
| 6 | Super Sterol Ester (Croda) | $C_{10-30}$ Cholesterol/Lanosterol Esters | 5.00% |
| 7 | Orisil 200 (Orisil) | Amorphous Fumed Silica | 1.00% |
| | Phase B | | |
| 8 | Ozokerite Wax SP-1020P (Strahl and Pitsch) | Ozokerite | 3.00% |
| 9 | Candelilla Wax SP-75 (Strahl and Pitsch) | *Euphorbia Cerifera* (Candelilla) Wax | 3.00% |
| 10 | Lexgard O (Inolex) | Caprylyl Glycol | 0.50% |
| 11 | Bronidox 1160 (BASF) | Phenoxyethanol | 0.50% |
| 12 | DL-Alpha Tocopheryl Acetate (DSM) | Tocopheryl Acetate | 0.10% |
| 13 | Pomegranate Blackberry FL OS 103-31160 (Bell Flavors and Fragrances) | Flavor | 0.50% |
| | Phase C | | |
| 14 | FAS55ERSI (KOBO) | Iron Oxides (CI77491), Cyclopentasiloxane, PEG/PPG 18/18 Dimethicone | 0.50% |
| | | Total | 100.00% |

Example 26

Degreasing Wipe Formulation

Provided here is a degreasing wipe formulation:

| | | Wipe | |
|---|---|---|---|
| Ingredient | Amount wt. % | | Application |
| Pentex 99 (DOSS) | 3.00 | Anionic Emulsifier | A wipe for tough soil hand cleaning. 1.2-2.2 g liq/g wipe |
| Tergitol 15-S-5 | 2.00 | Non-ionic emulsifier | |
| Example 2 | 2.75 | Solvent | |
| Deionized Water | 92.10 | Diluent | |
| Acticide SPX | 0.15 | Preservative | |

The formula of a degreasing wipe formulation incorporating Example 2 composition shown above (Hand Cleaner Towel Liquid LC#14100202) was tested for cleaning performance and speed of cleaning utilizing ASTM D4488-95-A6 (reapproved 2001) oil, carbon black and clay/white enamel painted stainless-steel panels test method. Cleaning performance and speed of cleaning were evaluated in comparison to commercially available hand cleaner towels.

Panel Preparation: Stainless steel sheeting was cut into 6 inch by 6 inch squares. The panels were cleaned with paper towel and acetone to remove any oil finish and dust from the panels. White semi-gloss paint was applied to cleaned panels. The panels were air dried for 7 hours and then placed in an oven at 54.5° C. for 16 hours. The panels were cooled at room temperature for 7 hours prior to use.

Soil Application: The panels were separately stained with the soil mixture by applying the soil to a paint applicator, which was then drawn across the prepared panel as many times as needed to get a consistent application of soil. The final soiled area was 2.5 inch wide and ran the length of the panel. The panels were then placed into an oven at 54.5° C. for 16 to 17 hours.

Colorimeter Measurements: After proper calibration of the Chroma Meter CR-410 Colorimeter, its data processor was set to the Y mode. For this test, it was only necessary to use the "Y" value. Reflectance of steel panels was read before and after soiling by taking 5 readings per panel perpendicularly across the grain of the test area. An average was calculated from the 5 readings and was used in the calculation of results.

Cleaning Test: The products were tested as received (RTU). The soiled panel was placed on Gardner Blue Straight-line Washability Machine and fastened to the base with a C-clamp. The test solution (10 mL) was applied onto a clean, damp cellulose sponge and inverted so that the wet side was in contact with the soiled panel and tested for the specified number of cycles. The panel was removed, rinsed lightly with cool tap water and air dried.

The cleaning efficiencies were calculated as follows:

% Cleaning Efficiency (C.E.)=(Rc−Rs)/(Ro−Rs)×100, wherein Rc is cleaned reflectance; Ro is original reflectance; and Rs is soiled reflectance.

The percent cleaning efficiencies and the number of cleaning cycles are shown below:

| Sample | Cycle # | Avg. C.E. % |
|---|---|---|
| Scrubs-in-a-bucket Hand Cleaner Towels LC#14-T0776 | 8 | 66.3 |
|  | 5 | 45.8 |
| Hand Cleaner Towel Liquid LC#141O0202 | 8 | 64.0 |
|  | 5 | 34.6 |

Figure 10A:
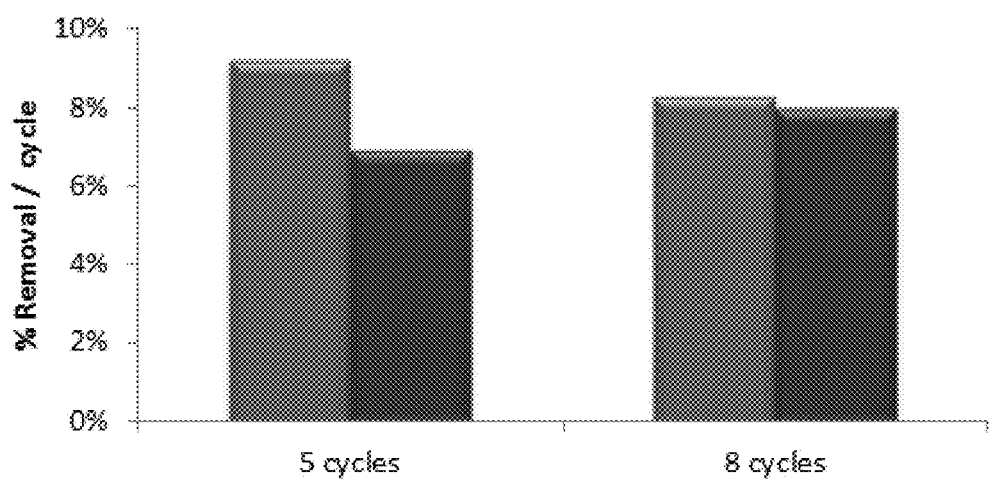
FIG. 10A illustrates a bar graph showing comparative cleaning efficiencies of a hand cleaner wipe according to one embodiment provided herein and a commercially available wipe formulation.
Figure 10B:
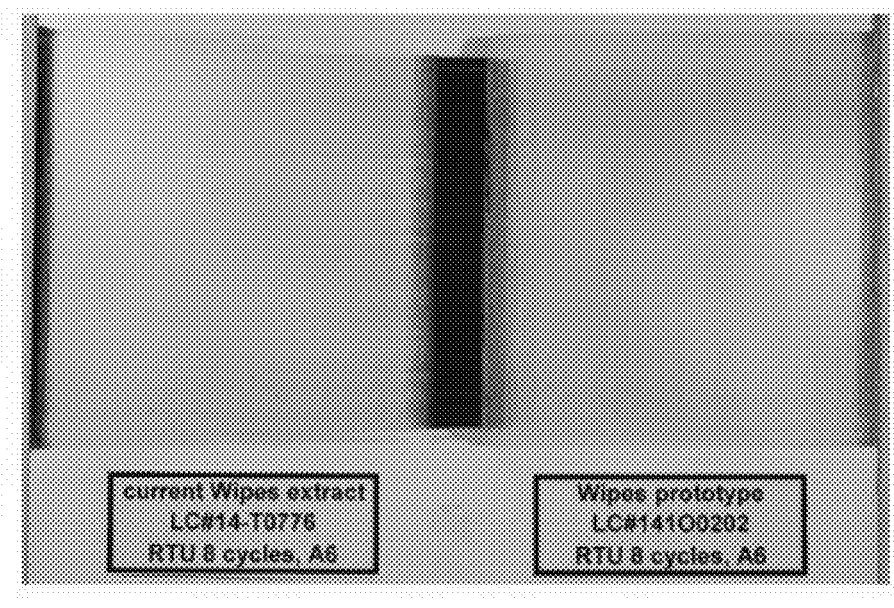
FIG. 10B illustrates a photograph showing cleaning efficiencies of hand cleaner wipe according to one embodiment provided herein and a commercially available wipe formulation.

FIG. 10A illustrates cleaning efficiencies of the hand cleaners shown in the above table as bar graphs. In FIG. 10A, each left bar in the set of two bars represents the cleaning efficiency of commercially available wipe extract obtained from Scrubs-in-a-bucket hand cleaner (LC#14-T0776) and each right bar in the set represents cleaning efficiency of the present cleaning product embodiment (hand cleaner towel liquid wipe prototype LC#14100202). The photograph shown in FIG. 10B illustrates that, after 8 cycles of cleaning, cleaning efficiencies were comparable between the present cleaning product embodiment and the commercially available formulation.

A degreasing wipe formulation shown above was also tested for cleaning performance and speed of cleaning as marker removers utilizing CSPA DCC-17 greasy soil test method. This method evaluates spray-and-wipe cleaners used on hard, non-glossy surfaces. Cleaning efficiency of present hand cleaner towel liquid LC#1400202 was evaluated in comparison to a commercially available and leading brand hand cleaner.

Panel Preparation: Masonite tiles were cleaned with a light duty dilution of hand dish detergent, and the panels were then rinsed and air dried.

Marker Application: A double application of each marker was applied in a uniform straight line along the long edge of the Masonite tile. The lines were spaced one inch apart. The soiled substrate was allowed to dry for four hours at room temperature.

Cleaning Test: For cleaning test, a clean cellulose sponge was conditioned for each cleaning procedure. A cleaner (10 mL) was dispensed onto the damp sponge to absorb the test solution. The sponge was placed so that the manufactured edge is the scrubbing surface. The tile was placed in the Gardner Blue Straight-line Washability Machine so that scrubbing action was perpendicular to the direction of the soiling. The wash apparatus was operated over the soiled area and scrubbing was continued for 50 cycles. The test area was rinsed with cool tap water.

Evaluation: A group of 3 panelists evaluated the tiles using the below rating system. An average of each rating is reported.
 5=total soil removal without streaking
 4=near total soil removal with streaking
 3=good soil removal
 2=moderate soil removal
 1=poor soil removal
 0=null soil removal

| Sample | Rating |
|---|---|
| Scrubs-in-a-bucket Hand Cleaner Towels LC#14-T0776 | 1 for black (approx. 5% removed)<br>2 for red (approx. 25% removed)<br>1 for blue (approx. 10% removed)<br>2 for green (approx. 25% removed) |
| Hand Cleaner Towel Liquid LC#141O0202 | 1 for black (less than 5% removed)<br>1 for red (approx. 10% removed)<br>1 for blue (approx. 5% removed)<br>2 for green (approx. 30% removed) |

Figure 11:
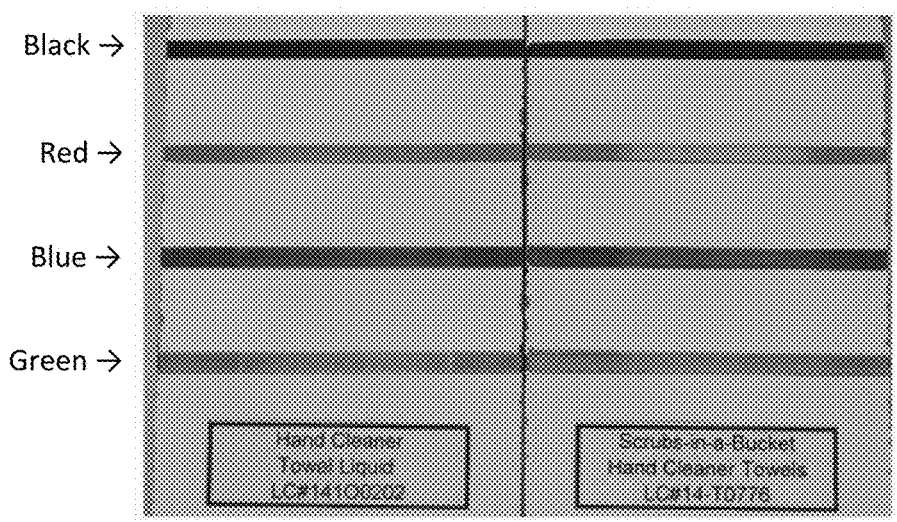
FIG. 11 illustrates a photograph of a panel with marker lines cleaned with a hand cleaner towel liquid according to one embodiment provided herein and a similarly soiled panel cleaned with a commercially available hand cleaner towel.

The photograph illustrating representative tiles cleaned with the hand cleaner towels shown in the above table is shown in FIG. 11.

Example 27

Comparison of Tar Soil Removal by Various Solvent Candidates

The following five solvent candidates were tested for their ability to remove tar soil: d-limonene, farnesene, a composition comprising mostly dihydrofarnesene (e.g., Example 9 composition), a composition comprising mostly hexahydrofarnesene (e.g., a composition comprising about 95 wt. % or more hexahydrofarnesene), and farnesane. In this experiment, a sample of Henry roofing adhesive 203 (weighing 0.5-0.9 grams) was transferred into a 20 mL vial, and the tar adhesive was allowed to air dry overnight. The solvent candidate was then added (10 mL/0.5 grams dried tar, adjusted for actual weight). The vial was capped and shaken manually for 10 minutes. The samples were then evaluated visually in the initial assessment, and the amount of material dissolved was estimated.

Figure 12:
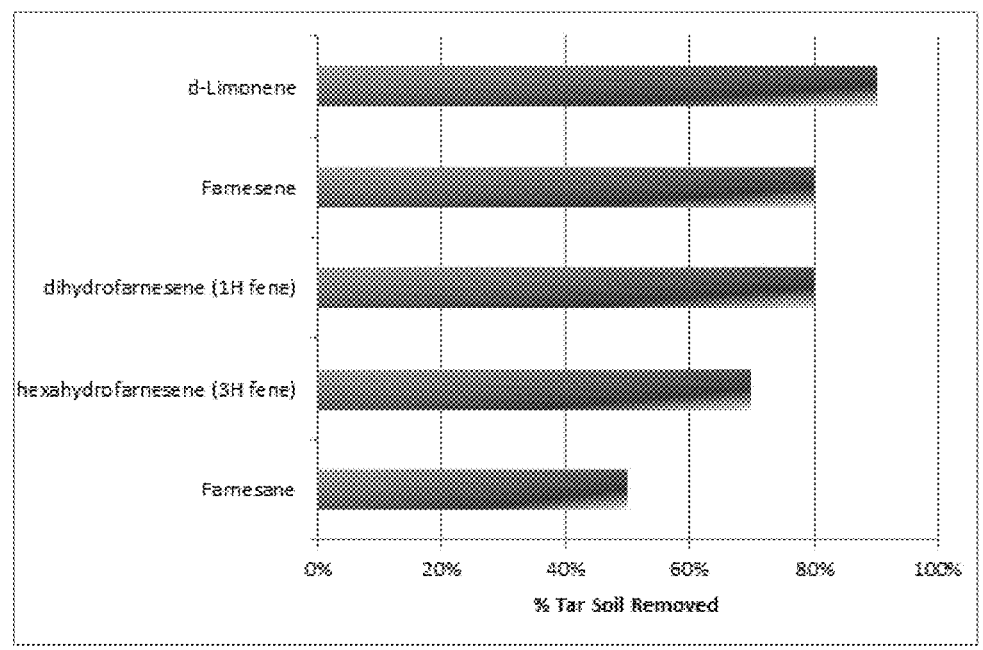
FIG. 12 illustrates the amount of tar soil removed by various solvents.

The results are shown in FIG. 12. As shown in FIG. 12, d-limonene is a good solvent candidate in terms of its cleaning performance. However, a solvent comprising 100 percent d-limonene does not meet the environmental regulatory requirements because of its VOC emission profile. In addition, the oxidative stability of d-limonene is less than that of the present solvent embodiment (e.g., Example 2 composition). Thus, an end product comprising a high percent amount of d-limonene is not ideal as a consumer product.

As shown in FIG. 12, both farnesene and dihydrofarnesene removed about 80 percent of tar soil. Thus, they are good solvent candidates. However, farnesene is prone to thermal instability, and therefore, farnesene is not ideal for use as a solvent compared to a composition comprising mostly dihydrofarnesene. Also, as shown in FIG. 12, farnesane and hexahydrofarnesene do not perform as well as dihydrofarnesene in removing tar soil.

These results indicate that the present compositions comprising a large amount of dihydrofarnesene are excellent solvent candidates, which are also VOC exempt because of their physical properties.

Example 28

Removal of Asphaltene and Grease Soils

Provided here are two exemplary compositions suitable for metal cleaning applications. It is noted that functional fluid 110 has the same ingredients as composition LC#142J2701 described above in Example 17. As shown below, Functional Fluid 110 includes Example 2 composition, and Functional Fluid 020 includes Example 9 composition.

Functional Fluid 110

| Ingredient | Amount wt. % | Function | Application |
|---|---|---|---|
| Example 2 | 9 | Solvent | A cleaner for removing crayon and pens from painted walls and interior surfaces |
| DBE-LVP | 9 | Solvent | |
| Rhodocal IPAM | 0.3 | Surfactant | |
| Isopar M | 81.7 | Solvent/Diluent | |
| d-Limonene | Optional 0-2% | Fragrance | |

Functional Fluid 020

| Ingredient | Amount wt. % | Application |
|---|---|---|
| Example 9 | 20 wt. % | Metal cleaning applications |
| LPA210 (Sasol) (paraffinic naphthenic solvent) | 80 wt. % | |

Functional Fluid 110 and Functional Fluid 020 have the following physical properties.

| | Functional Fluid 020 | Functional Fluid 110 | L142-Stoddard Solvent |
|---|---|---|---|
| Flash Point ° F. | 227 | 204 | 145 |
| Refractive Index (RI) | 1.4411 | 1.4688 | 1.4340 |
| Density | 0.823 | 0.823 | 0.803 |
| Viscosity cST @ 20° C. | 2.81 | 3.43 | 1.80 |

The compositions (i.e., Functional Fluid 110 and Functional Fluid 020) provide cost effective solutions appropriate for general and heavy duty machining, grinding, thread cleaning, and general metal cleaning. These compositions yield better cleaning performance on tough soils and provide better extended shelf life as compared to traditional metal working fluids.

Figures 13A, 13B:
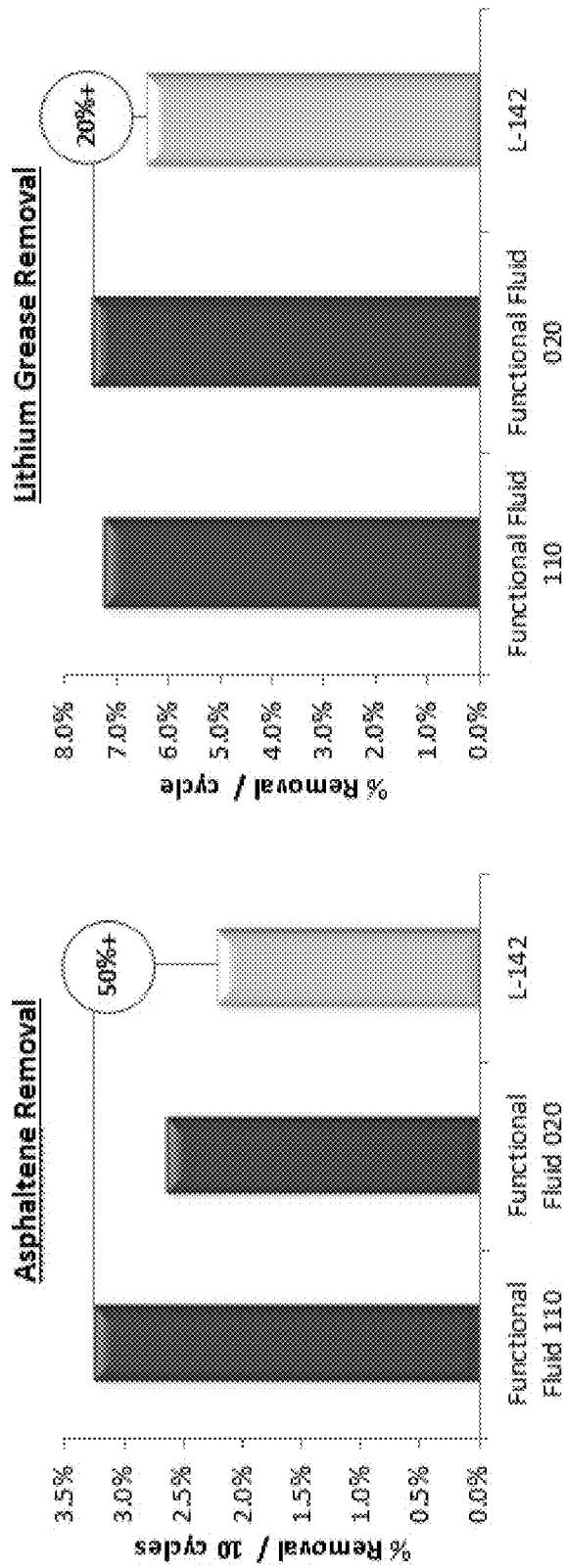
FIGS. 13A and 13B illustrate cleaning efficiencies of two different composition embodiments provided herein in comparison with commercially available product in removing asphaltene and lithium grease.

FIGS. 13A and 13B illustrate product performance data for Functional Fluid 020, Functional Fluid 110, and a commercially available product shown in the above table. The compositions were used to remove asphaltene and lithium grease based on ASTM D4488-95 Gardner straight-line coupon testing. FIGS. 13A and 13B illustrate the percent removal of asphaltene or lithium grease on substrates, respectively. As shown in FIGS. 13A and 13B, Functional Fluid 110 and Functional Fluid 020 overall delivered about 20 to 50% performance improvement as compared to traditional metal cleaning products, L142-Stoddard solvent. For example, as shown in FIG. 13A, the cleaning performance of Functional Fluid 110 in removing asphaltene was about 50% better than traditional metal cleaning product L142-Stoddard solvent. As shown in FIG. 13B, the cleaning performance of Functional Fluid 020 in removing lithium grease was about 20% better than L142-Stoddard solvent.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed is:

1. A composition comprising about 78 wt. % to about 97 wt. % dihydrofarnesene and about 20 wt. % to about 2 wt. % tetrahydrofarnesene, compared to the total amount of farnesene and farnesene derivatives in the composition, wherein the composition is substantially free of $C_4$ to $C_{10}$ volatile, organic oxygenated compounds, wherein the composition further comprises a stabilizer, which, when oxidized, does not form a quinone.

2. The composition of claim 1 that comprises about 83 wt. % to about 97 wt. % dihydrofarnesene and about 16 wt. % to about 2 wt. % tetrahydrofarnesene, compared to the total amount of farnesene and farnesene derivatives in the composition.

3. The composition of claim 1, wherein the composition comprises about 96 wt. % dihydrofarnesene compared to the total amount of farnesene and farnesene derivatives in the composition.

4. The composition of claim 1, further comprising about 0.1 wt. % to about 2 wt. % hexahydrofarnesene, compared to the total amount of farnesene and farnesene derivatives in the composition.

5. The composition of claim 1, further comprising less than about 0.1 wt. % farnesane, compared to the total amount of farnesene and farnesene derivatives in the composition.

6. The composition of claim 1, further comprising less than about 0.25 wt. % bisabolene, compared to the total amount of farnesene and farnesene derivatives in the composition.

7. The composition of claim 1, wherein the farnesene and farnesene derivatives comprise, on average, about 1.0 to about 1.25 double bonds per molecule of the farnesene and farnesene derivatives in the composition.

8. The composition of claim 1, wherein the farnesene and farnesene derivatives comprise, on average, about 1.1 to about 1.2 double bonds per molecule of the farnesene and farnesene derivatives in the composition.

9. The composition of claim 1, which is formulated as a solvent, a degreaser, a cleaning product, or a personal care product.

10. A composition comprising about 78 wt. % to about 97 wt. % dihydrofarnesene and about 20 wt. % to about 2 wt. % tetrahydrofarnesene, compared to the total amount of farnesene and farnesene derivatives in the composition, wherein the composition further comprises one or more additional components which are not reactants or reactant products produced by hydrogenation of farnesene; wherein the one or more additional components are selected from:
    a co-solvent selected from the group consisting of limonene, benzene, high flash aromatic naphtha, soy methyl ester, ethyl lactate, paraffins, dibasic esters, propylene glycol, ethyl alcohol, and a mixture thereof,
    a surfactant,
    water in an amount greater than 5 wt. % compared to the total weight of the composition,
    an emulsifier,
    an emollient,
    a thickener; and
    a mixture thereof.

11. The composition of claim 10 that comprises about 83 wt. % to about 97 wt. % dihydrofarnesene and about 16 wt. % to about 2 wt. % tetrahydrofarnesene, compared to the total amount of farnesene and farnesene derivatives in the composition.

12. The composition of claim 10, wherein the composition comprises about 96 wt. % dihydrofarnesene compared to the total amount of farnesene and farnesene derivatives in the composition.

13. The composition of claim 10, further comprising about 0.1 wt. % to about 2 wt. % hexahydrofarnesene, compared to the total amount of farnesene and farnesene derivatives in the composition.

14. The composition of claim 10, wherein the farnesene and farnesene derivatives comprise, on average, about 1.0 to about 1.25 double bonds per molecule of the farnesene and farnesene derivatives in the composition.

15. The composition of claim 10, wherein the co-solvent is limonene.

16. The composition of claim 10, wherein the one additional component is a surfactant.

17. The composition of claim 16, wherein the surfactant is selected from the group consisting of sodium lauryl ether sulfate, ethoxylated alcohol surfactant, fatty acid diethanolamine, orange oil emulsifier, acrylate-based emulsion copolymer, polyoxyethers of lauryl alcohol, linear isopropylamine dodecylbenzene sulfonate, blended alcohol ethoxylate, alkoxylated alcohol, sodium iminodipropionate, nonionic alcohol ethoxylates, a palm kernel alcohol ethoxylated and propoxylated surfactant, sodium xylene sulfonate, and a mixture thereof.

18. The composition of claim 10, wherein the one additional component is an emulsifier.

19. The composition of claim 18, wherein the emulsifier is selected from the group consisting of lauryl alcohol, fatty acid diethanolamine, ammonium methyl sulfate and fatty alcohol ethoxylate, linear alcohol ethoxylate, sodium branched dodecyl benzene sulfonate, and a mixture thereof.

20. The composition of claim 10, wherein the one additional component is an emollient.

21. The composition of claim 20, wherein the emollient is selected from the group consisting of fatty acids, alkyl ethoxylates, fatty acid ester ethoxylates, fatty alcohols, polysiloxanes, mucopolysaccharides, polyols, polysaccharides, urea derivatives, PPG-3 benzyl ether myristate, hydrogenated polyisobutene, butyelen/ethylene/styrene copolymer, ethylene/propylene/styrene copolymer, bis-diglyceryl polyacyladipate-2, pentaerythrityl tetraisostearate, $C^{10}$-$_{30}$ cholesterol/lanosterol esters, or a mixture thereof.

22. The composition of claim 10, wherein the one additional component is a thickener.

23. The composition of claim 22, wherein the thickener is selected from the group consisting of cellulosic thickeners, natural gums, acrylates, starches, stearates, fatty acid alcohols, clays, salts, candelilla wax, carnauba wax, beeswax, oils, linear alcohol ethoxylates, and a mixture thereof.

24. The composition of claim 10, wherein the composition further comprises at least one additive selected from the group consisting of a buffering agent, pH control agent, fragrance, flavor, defoamer, dye, whitener, brightener, solubilizing material, stabilizer, thickener, corrosion inhibitors, lotions, mineral oils, enzymes, cloud point modifiers, preservative, ion exchanger, chelating agent, sudsing control agent, soil removal agent, softening agent, opacifier, inert diluent, graying inhibitor, polymer, abrasive, exfoliant, and a mixture thereof.

25. A method of cleaning or degreasing a substrate or an object, the method comprising the step of contacting the substrate or the object with the composition of claim 10.

26. A method of producing a composition, the method comprising:
(a) reacting a composition comprising farnesene with hydrogen in the presence of a hydrogenation catalyst to produce a composition comprising about 60 wt. % to about 100 wt. % dihydrofarnesene, compared to the total amount of farnesene and farnesene derivatives; and
(b) filtering products of step (a) using an adsorbent to remove, volatile, organic oxygenated compounds; and
(c) adding a stabilizer, wherein the stabilizer, which, when oxidized, does not form a quinone.

27. The method of claim 26, wherein the adsorbent comprises alumina, silica, or a mixture thereof.

28. A composition produced by a method comprising:
(a) reacting a composition comprising farnesene with hydrogen in the presence of a hydrogenation catalyst to produce a composition comprising about 60 wt. % to about 100 wt. % dihydrofarnesene, compared to the total amount of farnesene and farnesene derivatives;
(b) filtering products of step (a) using an adsorbent to remove volatile, organic oxygenated compounds; and
(c) adding a stabilizer, wherein the stabilizer, which, when oxidized, does not form a quinone.

29. The composition of claim 28 that comprises about 78 wt. % to about 97 wt. % dihydrofarnesene and that further comprises about 20 wt. % to about 2 wt. % tetrahydrofarnesene, compared to the total amount of farnesene and farnesene derivatives.

30. The composition of claim 28 that comprises about 83 wt. % to about 97 wt. % dihydrofarnesene and that further comprises about 16 wt. % to about 2 wt. % tetrahydrofarnesene, compared to the total amount of farnesene and farnesene derivatives.

31. The composition of claim 28, wherein the composition further comprises about 0.1 wt. % to 2 wt. % hexahydrofarnesene, compared to the total amount of farnesene and farnesene derivatives.

32. The composition of claim 28, wherein the farnesene and farnesene derivatives comprise, on average, about 1.0 to about 1.25 double bonds per molecule of the farnesene and farnesene derivatives in the composition.

33. The composition of claim 28, wherein the stabilizer is butylated hydroxytoluene.

34. The composition of claim 28, wherein the stabilizer is present at a concentration of about 100 to 500 ppm.

35. The composition of claim 28, wherein the composition is substantially free of $C_4$ to $C_{10}$ volatile, organic oxygenated compounds.

36. The composition of claim 28, further comprising a co-solvent, surfactant, water, emulsifier, emollient, thickener, or a mixture thereof.

37. The composition of claim 10, wherein the surfactant is present in an amount greater than 5 wt. % compared to the total weight of the composition.

38. The composition of claim 10, wherein the co-solvent is present in an amount greater than 5 wt. % compared to the total weight of the composition.

* * * * *